(12) United States Patent
Jin et al.

(10) Patent No.: US 11,796,304 B2
(45) Date of Patent: Oct. 24, 2023

(54) SYSTEM AND METHOD FOR TRACKING A SHAPE

(71) Applicant: Carnegie Mellon University, Pittsburgh, PA (US)

(72) Inventors: Haojian Jin, Pittsburgh, PA (US); Jingxian Wang, Pittsburgh, PA (US); Swarun Kumar Suresh Kumar, Pittsburgh, PA (US); Jason I. Hong, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 597 days.

(21) Appl. No.: 17/050,010

(22) PCT Filed: Apr. 24, 2019

(86) PCT No.: PCT/US2019/028873
§ 371 (c)(1),
(2) Date: Oct. 23, 2020

(87) PCT Pub. No.: WO2019/209920
PCT Pub. Date: Oct. 31, 2019

(65) Prior Publication Data
US 2021/0180937 A1   Jun. 17, 2021

Related U.S. Application Data

(60) Provisional application No. 62/762,210, filed on Apr. 24, 2018.

(51) Int. Cl.
*G01B 7/287* (2006.01)
*G01B 7/16* (2006.01)
(Continued)

(52) U.S. Cl.
CPC ........... *G01B 7/287* (2013.01); *G01B 7/16* (2013.01); *G01S 13/75* (2013.01); *G01S 13/878* (2013.01); *G01S 13/89* (2013.01)

(58) Field of Classification Search
USPC ....................................................... 702/167
See application file for complete search history.

(56) References Cited

U.S. PATENT DOCUMENTS

| 2014/0327676 A1 | 11/2014 | House |
| 2015/0025788 A1 | 1/2015 | Crain et al. |

(Continued)

FOREIGN PATENT DOCUMENTS

WO   2019113441 A1   6/2019

OTHER PUBLICATIONS

"Bezier Curve", Wikipedia, pp. 1-9, http://web.archive.org/web/20170313055951/https://en.wikipedia.org/wiki/Bezier_curve, Mar. 13, 2017.

(Continued)

*Primary Examiner* — Paul D Lee
(74) *Attorney, Agent, or Firm* — THE WEBB LAW FIRM

(57) ABSTRACT

A method, system, and computer program product is provided for tracking the shape of a surface. The method includes generating a first plurality of surface models based on the surface, each surface model associated with surface parameter values and representing a different shape, determining an estimated position of the plurality of RF transponders on each surface model of the first plurality of surface models, communicating at least one activation signal to the plurality of RF transponders arranged on the surface, the surface comprising an unknown shape, receiving a plurality of response signals from at least a subset of the plurality of RF transponders, determining radio environment (Continued)

parameters for each surface model of the first plurality of surface models, and determining at least one selected surface model of the first plurality of surface models.

20 Claims, 13 Drawing Sheets

(51) Int. Cl.
    *G01S 13/75*         (2006.01)
    *G01S 13/87*         (2006.01)
    *G01S 13/89*         (2006.01)

(56) References Cited

U.S. PATENT DOCUMENTS

| | | | |
|---|---|---|---|
| 2015/0371104 A1 | 12/2015 | Fung et al. | |
| 2017/0188980 A1* | 7/2017 | Ash | A61B 5/744 |
| 2018/0192919 A1* | 7/2018 | Nakayama | A61B 5/1116 |
| 2019/0079176 A1* | 3/2019 | Weissman | H04B 17/318 |
| 2020/0375497 A1* | 12/2020 | Jin | A61B 5/1126 |

OTHER PUBLICATIONS

Ding et al., "FEMO: A Platform for Free-weight Exercise Monitoring with RFIDs", In Proceedings of the 13th ACM Conference on Embedded Networked Sensor Systems, Nov. 1-4, 2015, pp. 141-154.
Dementyev et al., "SensorTape: Modular and Programmable 3D-Aware Dense Sensor Network on a Tape", In Proceedings of the 28th Annual ACM Symposium on User Interface Software & Technology, Nov. 2015, pp. 1-11, https://www.researchgate.net/publication/301462154_SensorTape_Modular_and_Programmable_3D-Aware_Dense_Sensor_Network_on_a_Tape.
"Futures of the Scientific Imagination", National Science Foundation, 2017, pp. 1-6, https://www.nsf.gov/news/special_reports/futures/.
"Genetic algorithm", Wikipedia, pp. 1-10, https://web.archive.org/web/20171211190316/https://en.wikipedia.org/wiki/Genetic_algorithm, Dec. 11, 2017.
Hing N. Ng et al., "Computer Graphics Techniques for Modeling Cloth", Computer Graphics and Applications, 1996, pp. 28-41, vol. 16:5, IEEE.
Hou et al., "TagBreathe: Monitor Breathing with Commodity RFID Systems", In Distributed Computing Systems (ICDCS), 2017, pp. 1-10, IEEE.
Izadi et al., "KinectFusion: Real-time 3D Reconstruction and Interaction Using a Moving Depth Camera*", In proceedings of the 24th Annual ACM Symposium on User Interface Software and Technology, Oct. 16-19, 2011, pp. 1-10.
Jin et al., "Towards Wearable Everyday Body-Frame Tracking using Passive RFIDs", In proceedings of the ACM on Interactive, Mobile, Wearable and Ubiquitous Technologies, Dec. 2017, pp. 1-23, vol. 1: 4, Article 145.
Karrer et al., "Pinstripe: Eyes-free Continuous Input on Interactive Clothing", In Proceedings of the SIGCHI Conference on Human Factors in Computing Systems, May 7-12, 2011, pp. 1313-1322.
Lelthinger et al., "Jamming User Interfaces: Programmable particle stiffness and sensing for malleable and shape-changing devices", In Proceedings of the 25th annual ACM symposium on User interface software and technology, Oct. 2012, pp. 1-11, https://www.researchgate.net/publication/262399679_Jamming_user_interfaces_Programmable_particle_stiffness_and_sensing_for_malleable_and_shape-changing_devices.
Li et al., "ID-Match: A Hybrid Computer Vision and RFID System for Recognizing Individuals in Groups", 2016 CHI Conference, May 7-12, 2016, pp. 4933-4944.
Li et al., "IDSense: A Human Object Interaction Detection System Based on Passive UHF RFID", In proceedings of the 33rd Annual ACM Conference on Human Factors in Computing Systems, Apr. 18-23, 2015, pp. 1-10.

Ma et al., "Minding the Billions: Ultra-wideband Localization for Deployed RFID Tags", MobiCom '17, Oct. 16-20, 2017, pp. 1-13.
Millot et al., "An UWB Through-The-Wall Radar with 3D Imaging, Detection and Tracking Capabilities", European Radar Conference (EuRAD), Sep. 2015, pp. 1-4.
Moeslund et al., "A Survey of Computer Vision-Based Human Motion Capture", Computer Vision and Image Understanding, 2001, pp. 231-268, vol. 18.
"Motion Capture Systems by OptiTrack", Natural Point, 2011, pp. 1-2, https://web.archive.org/web/20140208010400/http://www.naturalpoint.com/optitrack/.
Neumann et al., "Lidar Imaging of Topography with Millimeter Ranging Precision for Proximity Science and Operations from Rovers or Spacecraft", pp. 1-2, 2017.
Ni et al., "LANDMARC: Indoor Location Sensing Using Active RFID*", pp. 1-10, 2004.
Occhiuzzi et al., "Modeling, Design and Experimentation of Wearable RFID Sensor Tag", IEEE Transactions on Antennas and Propagation, Aug. 2010, pp. 2490-2498, vol. 58:8.
Parzer et al., "SmartSleeve: Real-time Sensing of Surface and Deformation Gestures on Flexible, Interactive Textiles, using a Hybrid Gesture Detection Pipeline", In proceedings of the 30th Annual ACM Symposium on User Interface Software and Technology, Oct. 22-25, 2017, pp. 1-13.
Poupyrev et al., "Project Jacquard: Interactive Digital Textiles at Scale", In Proceedings of the 2016 CHI Conference on Human Factors in Computing Systems, May 7-12, 2016, pp. 4216-4227.
Rendl et al., "FlexSense: A Transparent Self-Sensing Deformable Surface", In Proceedings of the 27th annual ACM symposium on User interface software and technology, Oct. 2014, pp. 1-11, https://www.researchgate.net/publication/266477992_FlexSense_A_Transparent_Self-Sensing_Deformable_Surface.
Schneegass et al., "GestureSleeve: Using Touch Sensitive Fabrics for Gestural Input on the Forearm for Controlling Smartwatches", In proceedings of the ACM International Symposium on Wearable Computers, Sep. 12-16, 2016, pp. 108-115.
"SensorMania", Mediamatic, pp. 1-5, https://www.mediamatic.net/en/page/27491/sensormania, Jul. 7, 2011.
Shangguan et al., "Enabling Gesture-based Interaction with Objects", In proceedings of the 15th Annual International Conference on Mobile Systems, Applications and Services, Jun. 19-23, 2017, pp. 239-251.
Smiley, "RFID Readers For Mobile Phones From TSL", RFID Insider, Aug. 15, 2014, pp. 1-3, https://web.archive.org/web/20141107203441/http://blog.atlasrfidstore.com:80/rfid-readers-mobile-phones-tsl.
Terzopoulos et al., "Elastically Deformable Models", ACM Computer Graphics, Jul. 1987, pp. 205-214, vol. 21:4.
"The world's most widely used tracking library for augmented reality.", Artoolkit, pp. 1-4, https://web.archive.org/web/20171219083739/https://archive.artoolkit.org/, Dec. 19, 2017.
Walter et al., "Approximate Arc Length Parameterization", In proceedings of the 9th Brazilian Symposium on Computer Graphics and Image Processing, 1996, pp. 143-150.
Wang et al., "Arc-length Parameterized Spline curves for real-time simulation", In proceedings of the 5th International Conference on Curves and Surfaces, 2002, pp. 387-396.
Wang et al., "Fast Energy-Based Surface Wrinkle Modeling", Computers and Graphics pp. 1-24, 2006.
Wang et al., "RF-IDraw: Virtual Touch Screen in the Air Using RF Signals", In proceedings of the ACM SIGCOMM Computer Communication Review, Aug. 17-22, 2014, pp. 1-12.
Wei et al., "Gyro in the Air: Tracking 3D Orientation of Batteryless Internet-of-Things", In proceedings of the 22nd Annual International Conference on Mobile Computing and Networking, Oct. 3-7, 2016, pp. 1-14.
Xiong et al., "ArrayTrack: A Fine-Grained Indoor Location System", In proceedings of the 10th USENIX Symposium on Networked Systems Design and Implementation, 2013, pp. 71-84.
Yang et al., "Tagoram: Real-Time Tracking of Mobile RFID Tags to High Precision Using COTS Devices", In proceedings of the 20th Annual International Conference on Mobile Computing and Networking, Sep. 7-11, 2014, pp. 1-12.

(56) References Cited

OTHER PUBLICATIONS

Yao et al., "biologic: Natto Cells as Nanoactuators for Shape Changing Interfaces", In proceedings of the 33rd Annual ACM Conference on Human Factors in Computing Systems, Apr. 18-23, 2015, pp. 1-10.
Yao et al., "PneUI: Pneumatically Actuated Soft Composite Materials for Shape Changing Interfaces", In proceedings of the 26th Annual ACM Symposium on User Interface Software and Technology, Oct. 8-11, 2013, pp. 1-10.
Zhang et al., "Bridge-Deflection Estimation through Inclinometer Data Considering Structural Damages", Journal of Bridge Engineering, Oct. 2016, pp. 1-11.
Zhang et al., "Electrick: Low-Cost Touch Sensing Using Electric Field Tomography", In proceedings of the 2017 CHI Conference on Human Factors in Computing Systems, May 6-11, 2017, pp. 1-14.
Zhu et al., "Object Recognition and Navigation using a Single Networking Device", Jun. 19-23, 2017, pp. 1-13.

\* cited by examiner

SYSTEM AND METHOD FOR TRACKING A SHAPE

CROSS-REFERENCE TO RELATED APPLICATIONS

This application is the United States national phase of International Application No. PCT/US2019/028873 filed Apr. 24, 2019, and claims priority to U.S. Provisional Patent Application No. 62/762,210, filed Apr. 24, 2018, the disclosures of which are hereby incorporated by reference in their entirety.

GOVERNMENT LICENSE RIGHTS

This invention was made with Government support under CNS-1718435 awarded by the National Science Foundation. The Government has certain rights in the invention.

BACKGROUND

1. Field

This disclosure relates generally to shape tracking and, in non-limiting embodiments, systems, methods, and computer program products for tracking one or more shapes of a surface.

2. Technical Considerations

Detecting shapes of surfaces poses several technical challenges. Infrastructure-based solutions, such as depth cameras, function only in environments in which they are deployed and must be arranged within the line-of-sight to the surface being tracked. Structure-from-motion techniques in computer vision and RF imaging reconstruct the three-dimensional (3-D) surface of objects using images captured from multiple vantage points. Some vision-based systems use commodity cameras coupled with objects labeled with 3-D bar codes to accurately learn the shape of an object from a single image. There are also 3-D imaging solutions using ultra-wide band RADAR that require instrumenting the environment with multiple large antennas. Monitoring the structural integrity of large structural objects, such as bridges, requires specialized instruments such as inclinometers and highly-sensitive motion sensors.

Developing usable smart fabrics also presents technical challenges. Existing smart fabrics, such as those using conductive yarns, living cells, stretch-detecting bands, and fabric-based user interfaces, are restricted to specific types of inputs such as touch and humidity. These fabrics are unable to detect shapes.

Utilizing RF transponders to track objects requires the use of multiple reader antennas to perform triangulation. Using a single antenna reports only a single phase measurement per transponder, which may be insufficient to infer the coordinates for the transponder in 3-D space. The use of a single antenna has also been explored for shape determinations, but such systems have limitations and require fixed, static arrangements. There are no existing solutions for tracking the shape of an object in a portable manner that accounts for the multipath of signals.

SUMMARY

According to non-limiting embodiments or aspects, provided is a method for tracking a shape of a surface, the surface comprising a plurality of radio frequency (RF) transponders arranged thereon, the method comprising: generating, with at least one processor, a first plurality of surface models based on the surface, each surface model comprising surface parameter values and representing a different shape; determining, with at least one processor, an estimated position of the plurality of RF transponders on each surface model of the first plurality of surface models based on the surface model and a predetermined spatial arrangement of the plurality of RF transponders; communicating, with an antenna of a reader device, at least one activation signal to the plurality of RF transponders arranged on the surface, the surface comprising an unknown shape; receiving, with the antenna, a plurality of response signals from at least a subset of the plurality of RF transponders; determining, with at least one processor, radio environment parameters for each surface model of the first plurality of surface models based on the surface parameter values, the estimated position of the plurality of RF transponders, and the plurality of response signals; and determining, with at least one processor, at least one selected surface model of the first plurality of surface models based on the plurality of response signals and the radio environment parameters for the first plurality of surface models.

In non-limiting embodiments or aspects, the method further comprises: generating a second plurality of surface models based on the at least one selected surface model, each surface model of the second plurality of surface models comprising surface parameter values and representing a different shape; determining, with at least one processor, an estimated position of the plurality of RF transponders on each surface model of the second plurality of surface models based on the surface model and the predetermined spatial arrangement of the plurality of RF transponders; determining, with at least one processor, radio environment parameters for each surface model of the second plurality of surface models based on the surface parameter values, the estimated position of the plurality of RF transponders, and the plurality of response signals; and determining, with at least one processor, at least one second selected surface model of the second plurality of surface models based on the plurality of response signals and the radio environment parameters for the plurality of surface models.

In non-limiting embodiments or aspects, the surface parameter values for the second plurality of surface models are generated by mutating and/or crosslinking the at least one selected surface model. In non-limiting embodiments or aspects, the method further comprises predicting a surface geometry of the unknown shape based on the at least one selected surface model or a subsequent selected surface model from a subsequent plurality of surface models. In non-limiting embodiments or aspects, the method further comprises randomly generating the surface parameter values for the first plurality of surface models. In non-limiting embodiments or aspects, the surface parameter values for the first plurality of surface models are based on material properties of the surface. In non-limiting embodiments or aspects, wherein each surface model is represented as a function of the surface parameter values and defines at least one curve. In non-limiting embodiments or aspects, the radio environment parameters comprise phase shift. In non-limiting embodiments or aspects, the method further comprises arranging the plurality of RF transponders on the surface as a one-dimensional or two-dimensional array.

According to non-limiting embodiments or aspects, provided is a system for tracking a shape, comprising: a plurality of radio frequency (RF) transponders arranged on a surface adapted to be formed into a plurality of shapes; a reader device in communication with an antenna; and at least one processor in communication with the reader device, the at least one processor programmed and/or configured to: generate a first plurality of surface models based on the surface, each surface model comprising surface parameter values and representing a different shape; determine an estimated position of the plurality of RF transponders on each surface model of the first plurality of surface models based on the surface model and a predetermined spatial arrangement of the plurality of RF transponders; communicate, with the antenna, at least one activation signal to each RF transponder of the plurality of transponders arranged on the surface, the surface comprising an unknown shape; receive, with the antenna, a plurality of response signals from at least a subset of the plurality of RF transponders; determine radio environment parameters for each surface model of the first plurality of surface models based on the surface parameter values, the estimated position of the plurality of RF transponders, and the plurality of response signals; and determine at least one selected surface model of the first plurality of surface models based on the plurality of response signals and the radio environment parameters for the plurality of surface models.

In non-limiting embodiments or aspects, the at least one processor is further programmed or configured to: generate a second plurality of surface models based on the at least one selected surface model, each surface model of the second plurality of surface models comprising surface parameter values and representing a different shape; determine an estimated position of the plurality of RF transponders on each surface model of the second plurality of surface models based on the surface model and the predetermined spatial arrangement of the plurality of RF transponders; determine radio environment parameters for each surface model of the second plurality of surface models based on the surface parameter values, the estimated position of the plurality of RF transponders, and the plurality of response signals; and determine at least one second selected surface model of the second plurality of surface models based on the plurality of response signals and the radio environment parameters for the plurality of surface models.

In non-limiting embodiments or aspects, the surface parameter values for the second plurality of surface models are generated by mutating and/or crosslinking the at least one selected surface model. In non-limiting embodiments or aspects, the at least one processor is further programmed or configured to predict a surface geometry of the unknown shape based on the at least one selected surface model or a subsequent selected surface model from a subsequent plurality of surface models. In non-limiting embodiments or aspects, the at least one processor is further programmed or configured to randomly generate the surface parameter values for the first plurality of surface models. In non-limiting embodiments or aspects, the surface parameter values for the first plurality of surface models are based on material properties of the surface. In non-limiting embodiments or aspects, each surface model is represented as a function of the surface parameter values and defines at least one curve. In non-limiting embodiments or aspects, the radio environment parameters comprise phase shift. In non-limiting embodiments or aspects, the plurality of RF transponders are arranged on the surface as a one-dimensional or two-dimensional array.

According to non-limiting embodiments or aspects, provided is a computer program product for tracking a shape, wherein a plurality of radio frequency (RF) transponders are arranged on a surface adapted to be formed into a plurality of shapes, comprising at least one non-transitory computer-readable medium including program instructions that, when executed by at least one processor, cause the at least one processor to: generate a first plurality of surface models based on the surface, each surface model comprising surface parameter values and representing a different shape; determine an estimated position of the plurality of RF transponders on each surface model of the first plurality of surface models based on the surface model and a predetermined spatial arrangement of the plurality of RF transponders; receive a plurality of signals from at least a subset of the plurality of RF transponders; determine radio environment parameters for each surface model of the first plurality of surface models based on the surface parameter values, the estimated position of the plurality of RF transponders, and the plurality of signals; and determine at least one selected surface model of the first plurality of surface models based on the plurality of response signals and the radio environment parameters for the plurality of surface models.

In non-limiting embodiments or aspects, the program instructions further cause the at least one processor to: generate a second plurality of surface models based on the at least one selected surface model, each surface model of the second plurality of surface models comprising surface parameter values and representing a different shape; determine an estimated position of the plurality of RF transponders on each surface model of the second plurality of surface models based on the surface model and the predetermined spatial arrangement of the plurality of RF transponders; determine radio environment parameters for each surface model of the second plurality of surface models based on the surface parameter values, the estimated position of the plurality of RF transponders, and the plurality of response signals; and determine at least one second selected surface model of the second plurality of surface models based on the plurality of response signals and the radio environment parameters for the plurality of surface models.

Other non-limiting embodiments or aspects will be set forth in the following numbered clauses:

Clause 1: A method for tracking a shape of a surface, the surface comprising a plurality of radio frequency (RF) transponders arranged thereon, the method comprising: generating, with at least one processor, a first plurality of surface models based on the surface, each surface model comprising surface parameter values and representing a different shape; determining, with at least one processor, an estimated position of the plurality of RF transponders on each surface model of the first plurality of surface models based on the surface model and a predetermined spatial arrangement of the plurality of RF transponders; communicating, with an antenna of a reader device, at least one activation signal to the plurality of RF transponders arranged on the surface, the surface comprising an unknown shape; receiving, with the antenna, a plurality of response signals from at least a subset of the plurality of RF transponders; determining, with at least one processor, radio environment parameters for each surface model of the first plurality of surface models based on the surface parameter values, the estimated position of the plurality of RF transponders, and the plurality of response signals; and determining, with at least one processor, at least one selected surface model of the first plurality of surface models based on the plurality of response signals and the radio environment parameters for the first plurality of surface models.

Clause 2: The method of clause 1, further comprising: generating a second plurality of surface models based on the at least one selected surface model, each surface model of the second plurality of surface models comprising surface parameter values and representing a different shape; determining, with at least one processor, an estimated position of the plurality of RF transponders on each surface model of the second plurality of surface models based on the surface model and the predetermined spatial arrangement of the plurality of RF transponders; determining, with at least one processor, radio environment parameters for each surface model of the second plurality of surface models based on the surface parameter values, the estimated position of the plurality of RF transponders, and the plurality of response signals; and determining, with at least one processor, at least one second selected surface model of the second plurality of surface models based on the plurality of response signals and the radio environment parameters for the plurality of surface models.

Clause 3: The method of clauses 1 or 2, wherein the surface parameter values for the second plurality of surface models are generated by mutating and/or crosslinking the at least one selected surface model.

Clause 4: The method of any of clauses 1-3, further comprising predicting a surface geometry of the unknown shape based on the at least one selected surface model or a subsequent selected surface model from a subsequent plurality of surface models.

Clause 5: The method of any of clauses 1-4, further comprising randomly generating the surface parameter values for the first plurality of surface models.

Clause 6: The method of any of clauses 1-5, wherein the surface parameter values for the first plurality of surface models are based on material properties of the surface.

Clause 7: The method of any of clauses 1-6, wherein each surface model is represented as a function of the surface parameter values and defines at least one curve.

Clause 8: The method of any of clauses 1-7, wherein the radio environment parameters comprise phase shift.

Clause 9: The method of any of clauses 1-8, further comprising arranging the plurality of RF transponders on the surface as a one-dimensional or two-dimensional array.

Clause 10: A system for tracking a shape, comprising: a plurality of radio frequency (RF) transponders arranged on a surface adapted to be formed into a plurality of shapes; a reader device in communication with an antenna; and at least one processor in communication with the reader device, the at least one processor programmed and/or configured to: generate a first plurality of surface models based on the surface, each surface model comprising surface parameter values and representing a different shape; determine an estimated position of the plurality of RF transponders on each surface model of the first plurality of surface models based on the surface model and a predetermined spatial arrangement of the plurality of RF transponders; communicate, with the antenna, at least one activation signal to each RF transponder of the plurality of transponders arranged on the surface, the surface comprising an unknown shape; receive, with the antenna, a plurality of response signals from at least a subset of the plurality of RF transponders; determine radio environment parameters for each surface model of the first plurality of surface models based on the surface parameter values, the estimated position of the plurality of RF transponders, and the plurality of response signals; and determine at least one selected surface model of the first plurality of surface models based on the plurality of response signals and the radio environment parameters for the plurality of surface models.

Clause 11: The system of clause 10, wherein the at least one processor is further programmed or configured to: generate a second plurality of surface models based on the at least one selected surface model, each surface model of the second plurality of surface models comprising surface parameter values and representing a different shape; determine an estimated position of the plurality of RF transponders on each surface model of the second plurality of surface models based on the surface model and the predetermined spatial arrangement of the plurality of RF transponders; determine radio environment parameters for each surface model of the second plurality of surface models based on the surface parameter values, the estimated position of the plurality of RF transponders, and the plurality of response signals; and determine at least one second selected surface model of the second plurality of surface models based on the plurality of response signals and the radio environment parameters for the plurality of surface models.

Clause 12: The system of clauses 10 or 11, wherein the surface parameter values for the second plurality of surface models are generated by mutating and/or crosslinking the at least one selected surface model.

Clause 13: The system of any of clauses 10-12, wherein the at least one processor is further programmed or configured to predict a surface geometry of the unknown shape based on the at least one selected surface model or a subsequent selected surface model from a subsequent plurality of surface models.

Clause 14: The system of any of clauses 10-13, wherein the at least one processor is further programmed or configured to randomly generate the surface parameter values for the first plurality of surface models.

Clause 15: The system of any of clauses 10-14, wherein the surface parameter values for the first plurality of surface models are based on material properties of the surface.

Clause 16: The system of any of clauses 10-15, wherein each surface model is represented as a function of the surface parameter values and defines at least one curve.

Clause 17: The system of any of clauses 10-16, wherein the radio environment parameters comprise phase shift.

Clause 18: The system of any of clauses 10-17, wherein the plurality of RF transponders are arranged on the surface as a one-dimensional or two-dimensional array.

Clause 19: A computer program product for tracking a shape, wherein a plurality of radio frequency (RF) transponders are arranged on a surface adapted to be formed into a plurality of shapes, comprising at least one non-transitory computer-readable medium including program instructions that, when executed by at least one processor, cause the at least one processor to: generate a first plurality of surface models based on the surface, each surface model comprising surface parameter values and representing a different shape; determine an estimated position of the plurality of RF transponders on each surface model of the first plurality of surface models based on the surface model and a predetermined spatial arrangement of the plurality of RF transponders; receive a plurality of signals from at least a subset of the plurality of RF transponders; determine radio environment parameters for each surface model of the first plurality of surface models based on the surface parameter values, the estimated position of the plurality of RF transponders, and the plurality of signals; and determine at least one selected surface model of the first plurality of surface models based on the plurality of response signals and the radio environment parameters for the plurality of surface models.

Clause 20: The computer program product of clause 19, wherein the program instructions further cause the at least one processor to: generate a second plurality of surface models based on the at least one selected surface model, each surface model of the second plurality of surface models comprising surface parameter values and representing a different shape; determine an estimated position of the plurality of RF transponders on each surface model of the second plurality of surface models based on the surface model and the predetermined spatial arrangement of the plurality of RF transponders; determine radio environment parameters for each surface model of the second plurality of surface models based on the surface parameter values, the estimated position of the plurality of RF transponders, and the plurality of response signals; and determine at least one second selected surface model of the second plurality of surface models based on the plurality of response signals and the radio environment parameters for the plurality of surface models.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Additional advantages and details are explained in greater detail below with reference to the exemplary embodiments that are illustrated in the accompanying schematic figures, in which.

DESCRIPTION OF THE PREFERRED EMBODIMENTS

Figure 1:
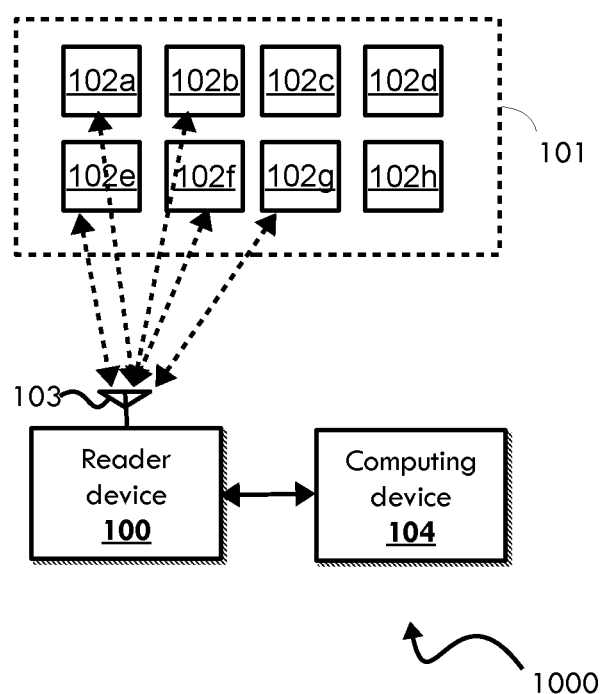
FIG. 1 is a schematic diagram of a system for tracking a shape according to a non-limiting embodiment.

For purposes of the description hereinafter, the terms "end," "upper," "lower," "right," "left," "vertical," "hori- zontal," "top," "bottom," "lateral," "longitudinal," and derivatives thereof shall relate to the embodiments as they are oriented in the drawing figures. However, it is to be understood that the embodiments may assume various alternative variations and step sequences, except where expressly specified to the contrary. It is also to be understood that the specific devices and processes illustrated in the attached drawings, and described in the following specification, are simply exemplary embodiments or aspects of the invention. Hence, specific dimensions and other physical characteristics related to the embodiments or aspects disclosed herein are not to be considered as limiting.

No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Furthermore, as used herein, the term "set" is intended to include one or more items (e.g., related items, unrelated items, a combination of related and unrelated items, and/or the like) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like, of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit processes information received from the first unit and communicates the processed information to the second unit.

As used herein, the term "computing device" may refer to one or more electronic devices configured to process data. A computing device may, in some examples, include the necessary components to receive, process, and output data, such as a display, a processor, a memory, an input device, and a network interface. A computing device may be a mobile device. As an example, a mobile device may include a cellular phone (e.g., a smartphone or standard cellular phone), a portable computer, a wearable device (e.g., watches, glasses, lenses, clothing, and/or the like), a personal digital assistant (PDA), and/or other like devices. The computing device may also be a desktop computer or other form of non-mobile computer.

FIG. 1 depicts a system 1000 for tracking a shape of a surface according to a non-limiting embodiment. The system 1000 includes a reader device 100 and a plurality of radio frequency (RF) transponders 102a-h arranged on a surface 101. The surface 101 may be comprised of any material or combination of materials. The surface 101 may be shapeable in that the surface 101 may be adapted (e.g., arranged, manipulated, deformed, depressed, bent, stretched, stressed, compressed, reconfigured, etc.) into a plurality of different shapes. A surface may be substantially one-dimensional (1-D), such as a string or wire, two-dimensional (2-D), such as a garment or carpet, or three-dimensional (3-D), such as a curved object. In non-limiting embodiments, the RF transponders 102a-h are passive RF transponders that are arranged on one or more surfaces (e.g., affixed to the surface, integrated with the surface, and/or the like). The surface may form any type of object or portion of object capable of forming different shapes, such as an article of clothing, a carpet, a toy, a tool, a building, a bridge, and/or the like. The RF transponders 102a-h are pictured in FIG. 1 as a 2-D array (2×4), although it will be appreciated that, in some non-limiting embodiments, the plurality of RF transponders 102a-h may be arranged in a 1-D array or in any other manner. Any number of RF transponders 102a-h may be used. The arrangement of RF transponders 102a-h is predetermined and known for the surface 101 when the surface 101 is in a predetermined shape (e.g., flat, straight, planar, a default configuration, etc.).

In non-limiting embodiments, the RF transponders 102a-h may be lightweight, machine-washable, battery-free, and ultra-high frequency (UHF) such that they can be incorporated into a usable material without restricting use of the material. For example, in non-limiting embodiments, each RF transponder 102a-h may include a limited amount of memory and therefore may contain a 96-bit or 128-bit serial number, rather than the 2 kilobytes of data that is sometimes included with RF transponders having Electronic Product Code (EPC) memory. In some non-limiting embodiments, the RF transponders may be constructed with conductive yarns woven directly into the surface 101. It will be appreciated by those skilled in the art that any RF transponders may be used, with or without EPC memory, of different shapes, sizes, and manufacture.

With continued reference to FIG. 1, the reader device 100 may include any device having an antenna 103 (or in communication with an antenna 103) and a processor and/or circuitry for activating and communicating with the plurality of passive RF transponders 102a-h. In non-limiting embodiments, the reader device 100 is a single-antenna handheld RFID-reader. In some non-limiting embodiments, the reader device 100 may also include a battery that can be periodically recharged. In some non-limiting embodiments, the reader device 100 may be a multi-purpose computing device, such as a mobile device (e.g., a smartphone or portable computing device), configured with software and/or circuitry to transmit one or more activation signals, receive a plurality of response signals, and process the received signals. It will be appreciated that the reader device 100 may include any device capable of communicating with RF transponders 102a-h. Although the reader device 100 may include a plurality of antennas in some non-limiting embodiments, it will be appreciated that in such embodiments only one antenna needs to be used by the reader device 100 to communicate with the RF transponders 102a-h. The antenna 101 may be internal or external to the reader device 100.

Still referring to FIG. 1, the reader device 100 is in communication with a computing device 104. In some non-limiting embodiments, the reader device 100 may be part of or integrated with the computing device 104, such as a mobile device that includes hardware and/or software for interrogating RF transponders using an antenna. In other non-limiting embodiments, the computing device 104 may be independent from the reader device 100 and may communicate with the reader device 100 via a wired or wireless connection. Various other arrangements are possible.

With continued reference to FIG. 1, in non-limiting embodiments the reader device 100 may be arranged on the surface 101, on an associated object, or may be located anywhere else within range of the RF transponders 102a-h. The reader device 100 may be fixed or may move relative to the surface 101. For example, the reader device 100 may be located in a user's pocket, attached to an article of clothing, placed on a table or floor, and/or the like. The reader device 100 and RF transponders 102a-h may move relative to each other at unknown trajectories. The reader device 100, using the antenna 103, communicates one or more activation signals configured to activate the passive RF transponders 102a-h. The activation signal(s) energize each of the passive RF transponders 102a-h which, in response to being energized, emit one or more response signals. The one or more response signals are received by the antenna 103 of the reader device 100 and communicated to the computing device 104. Each of the RF transponders 102a-h are located at separate distances from the reader device 100. Each distance (e.g., an actual distance or a relative distance) may be determined by the computing device 104 based on an amount of time it takes for the response signals to be received by the reader device 100. As an example, the computing device 104 may determine a distance of each RF transponder 102a-h based on a phase of each of the response signals. In non-limiting embodiments, the reader device 100 and/or computing device 104 may support detecting the phase of the response signals. Various other arrangements are possible.

Still referring to FIG. 1, the reader device 100 may distinguish between response signals and therefore between RF transponders 102a-h based on a modulation of each of the response signals. For example, each RF transponder 102a-h may be configured to modulate the response signals (e.g., backscatter signals) using ON-OFF keying by changing an impedance of a respective antenna of the RF transponder. The reader device 100, in response to receiving the response signals, may then demodulate each response signal to determine which response signal came from which RF transponder 102a-h based on a predefined modulation schema. It will be appreciated that various other methods may be used for uniquely identifying the response signals at the reader device 100. For example, in some non-limiting embodiments, a unique identifier corresponding to each RF transponder may be packaged in a respective response signal as a header or otherwise as part of the communicated data.

With continued reference to FIG. 1, in non-limiting embodiments the parameters defining the arrangement of RF transponders 102a-h (e.g., transponder layout information), such as, but not limited to, a predefined spacing between RF transponders, a location of each RF transponder on the surface 101, expected modulation patterns, material properties, and/or the like, may be predefined and stored in memory that is accessible to the reader device 100 or the computing device 104 that processes the signals. For example, the transponder layout information may be stored in a network-accessible database such that the layout can be identified based on unique identifiers or modulations associated with the RF transponders. In some non-limiting embodiments, the transponder layout information may also be stored in EPC memory in one or each of the RF transponders. It will be appreciated that various other arrangements for storing transponder layout information may be used.

In non-limiting embodiments, and still referring to FIG. 1, the computing device 104 tracks the shape of the surface 101 without localizing individual RF transponders 102a-h by implementing mathematical models (e.g., higher-order Bézier curves) of surfaces that represent the surfaces with formulas having a limited number of unknown coefficients. The computing device 104 optimizes the unknown coefficients that best fit the measurements obtained from response signals received from the RF transponders 102a-h. By directly optimizing for surface coefficients, rather than attempting to locate the location of each RF transponder 102a-h, the computing device 104 reduces the number of variables necessary for determining a shape of the surface 101 and, as a result, reduces the amount of computational resources needed to determine the shape.

Figure 2A:
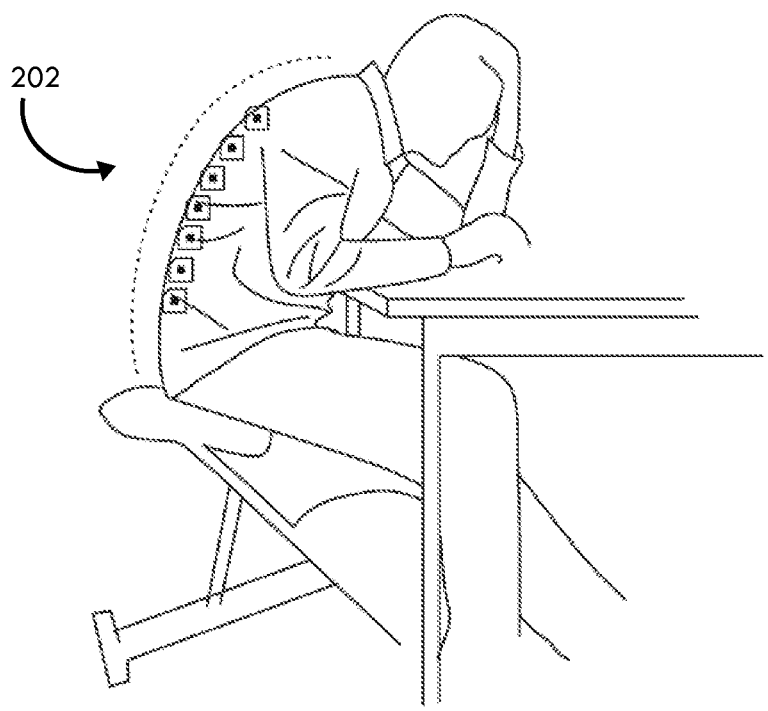
FIGS. 2A-2D illustrate different arrangements of RF transponders according to non-limiting embodiments.

Referring now to FIGS. 2A-2D, various arrangements of RF transponders are shown on different surfaces according to non-limiting embodiments. In the arrangement shown in FIG. 2A, an array of RF transponders 202 is arranged on an article of clothing or directly on a person's body to measure and track the curvature of a person's body (e.g., spine). Such an arrangement allows for the system to track a posture of a user in real-time or near-real-time during day-to-day activities or specific activities. The RF transponders may be integrated into an article of clothing and/or may be arranged otherwise on the body. Although FIG. 2A shows an arrangement on a spine of a person, it will be appreciated that one or more body parts may be tracked with the system 1000 including, but not limited to, the chest (e.g., to measure breathing), arms and legs (e.g., to measure muscle usage), and/or the like. Moreover, it will be appreciated that a reader device (not shown in FIG. 2A) may be arranged in the user's pocket, on a table or other surface, or elsewhere within range of the transponders 202 arranged on the person's body or clothing.

Figure 2B:
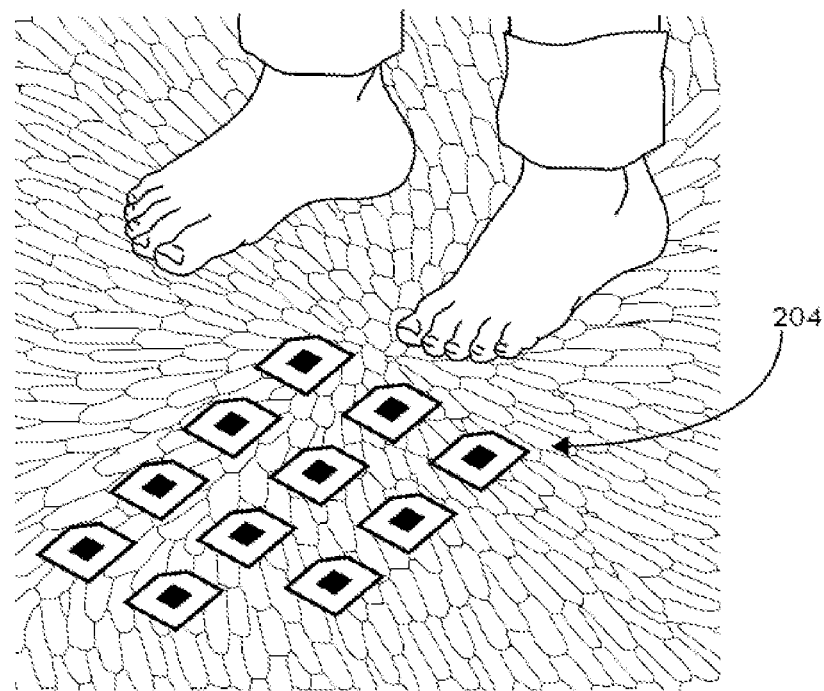

FIG. 2B shows an array of RF transponders 204 on a carpet or other shapeable floor surface, such as a mat, floor board, and/or the like. By tracking changes in the shape of the floor surface, the system is able to track the presence, location, and/or weight of people and/or objects on the floor surface by tracking deformations in the floor surface. A reader device (not shown in FIG. 2B) may be in a person's pocket or otherwise arranged on a body, on a floor or other surface, or elsewhere within range of the RF transponders 204 arranged on the floor surface.

Figure 2C:
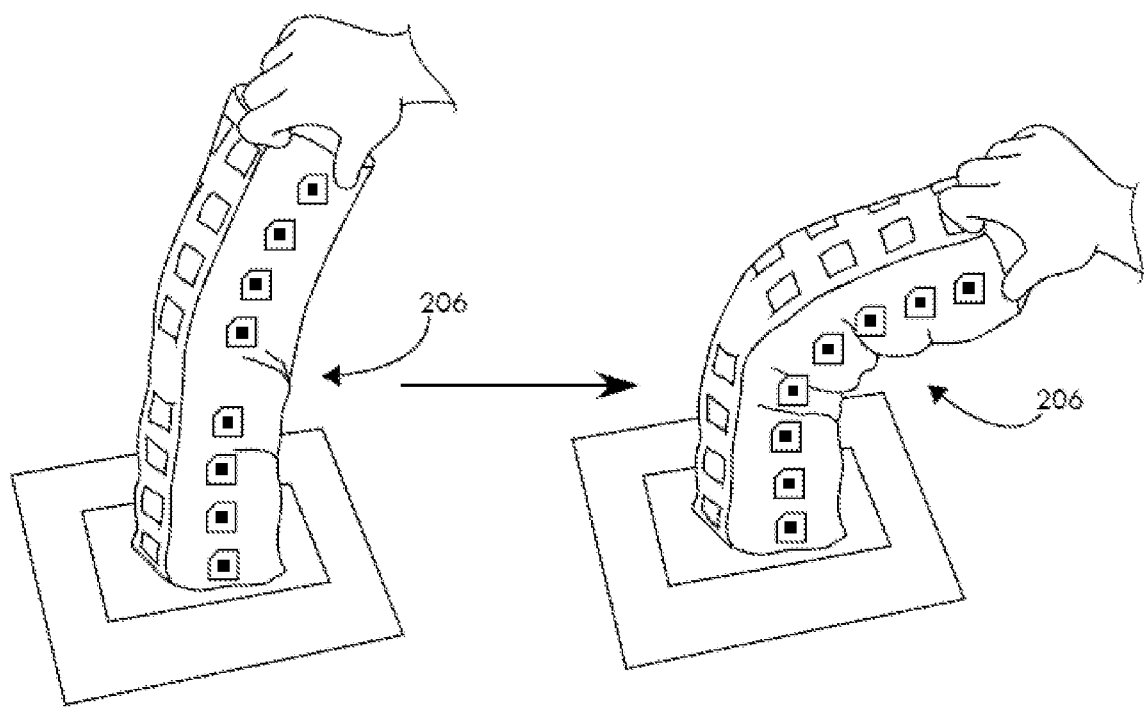

FIG. 2C shows an array of RF transponders 206 on a toy that is being actively deformed from a first shape to a second shape. By tracking changes in the shape of a malleable toy, different responses (e.g., lights, sounds, games, etc.) can be provided depending upon where the toy is touched, depressed, squeezed, etc., and by what level of force. As an example, an array of RF transponders 206 on or integrated with a plush toy (e.g., a stuffed animal, a doll, etc.) may allow for different outputs depending on whether it is hugged, dropped, squeezed, and/or the like. Further, interactive toys may be provided with RF transponders to generate visual renderings on a computing device based on the shape of an object.

Figure 2D:
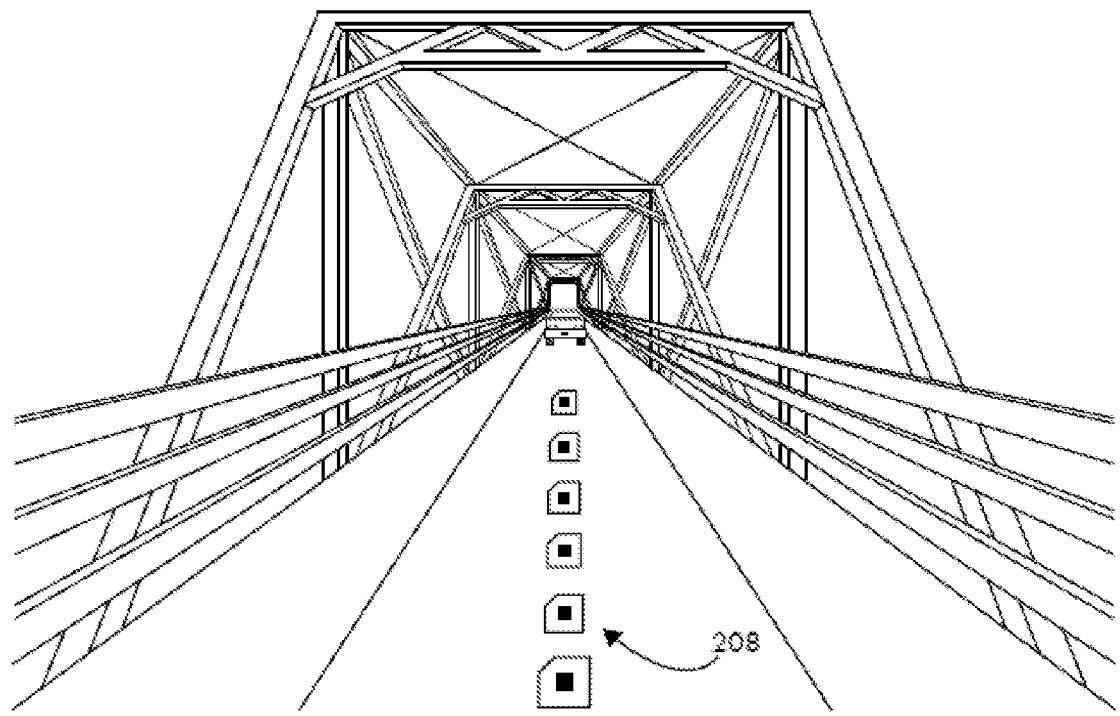

FIG. 2D shows an array of RF transponders 208 on a bridge. By tracking changes in the shape of a bridge or other architectural structure, sags, vibrations, loads, and/or other like attributes of the structure may be identified and remedied. It will be appreciated that RF transponders may be arranged in a line (e.g., a 1-D array) on a bridge to obtain a 2-D curve or, in other embodiments, may be arranged in a 2-D array to obtain additional shape information. Likewise with a building, RF transponders may be arranged vertically along the sides of a building, across floors and/or ceilings, and/or the like. It will be appreciated that the shape of any portion of a structure may be tracked.

Figure 3:
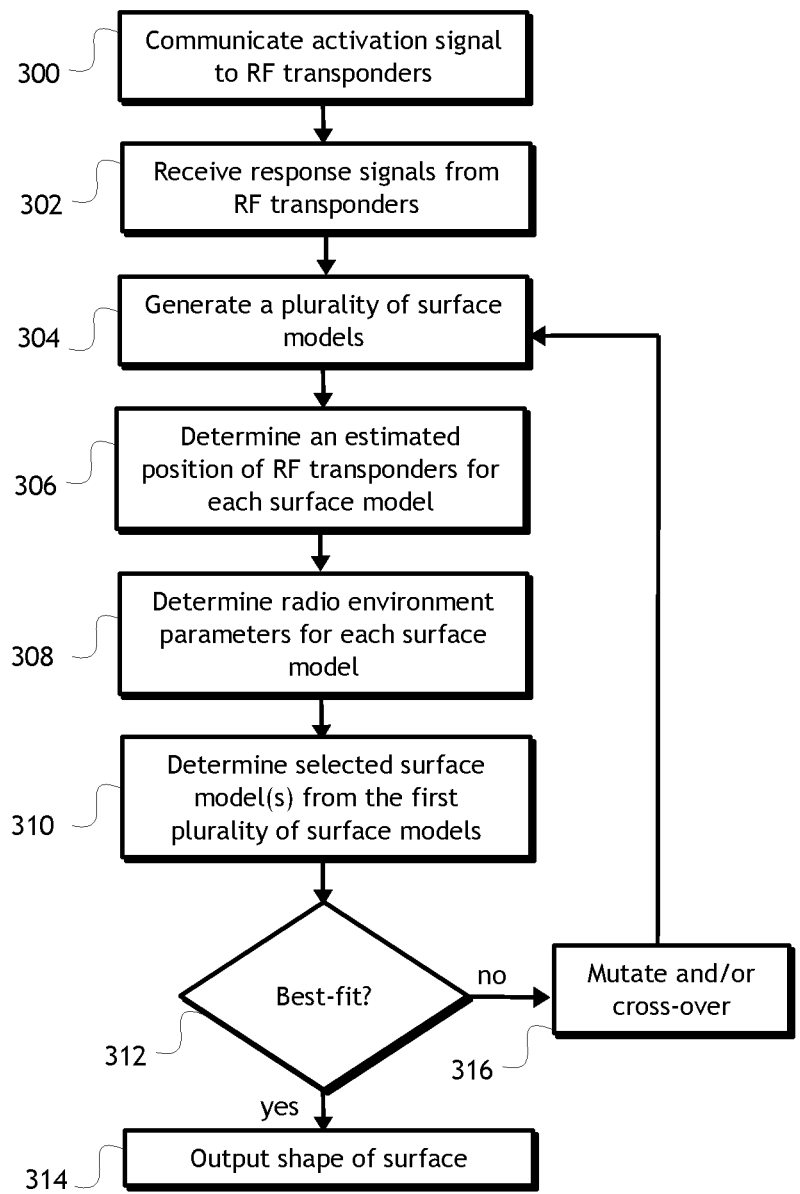
FIG. 3 is a flow diagram for a method of tracking a shape according to a non-limiting embodiment.

Referring now to FIG. 3, a method for tracking a shape is shown according to a non-limiting embodiment. It will be appreciated that the order of the steps shown in FIG. 3 is for illustration purposes only and that non-limiting embodiments may involve more steps, fewer steps, different steps, and/or a different order of steps. The method may begin at step 300 in which an activation signal is transmitted from an antenna of a reader device to a plurality of RF transponders arranged on a surface. The activation signal may be communicated in a manner to energize a plurality of RF transponders within range of the antenna such that the transponders communicate a response signal in response to being energized. At step 302, the antenna receives at least one response signal from each of a plurality of transponders. In some examples, several signals are received from each transponder via multiple paths. In some examples, the plurality of transponders that respond may be less than the total number of RF transponders due to signal occlusion or other errors. The shape of the surface when the transponders communicate the response signals (e.g., a current shape) is the shape that the method determines and outputs at step 314. In some non-limiting embodiments, steps 300 and 302 may be performed subsequent to step 304.

With continued reference to FIG. 3, at step 304 a plurality of surface models is generated for the surface being tracked. An initial performance of step 304 may result in a first generation (e.g., a first plurality) of surface models for use in a genetic natural selection algorithm. The surface parameters that define a surface geometry of each surface model may be randomly generated within constraining parameters based on material properties of the surface, such as stretch, bend, elasticity, and/or the like. The surface models are based on a model represented by the formula $S(p)=0$, where p represents a set of surface parameters that define the surface geometry. For a given material and/or surface, and the range of shapes that one wishes to track, $S(p)$ may be developed to mathematically represent the geometry of the surface in 2-D or 3-D space. The surface parameters may be constrained to allow for surfaces that stretch or curve to the extent that the material(s) of which the surface is comprised can adapt. By choosing functions $S(p)$ that succinctly express surfaces using a minimal number of surface parameters, the size of the value p (representing the surface parameters) may be significantly smaller than the number of RF transponders on the surface. As a result, the algorithm optimizes for p to fit the observed signals, even if there is only one channel measurement per RF transponder.

Reducing the number of surface parameters can improve the computational performance and avoid potential overfitting (e.g., iterating through more generations than necessary). A shape representation may capture various material properties, e.g., elongation, stiffness, and/or the like, and is intuitive for real world applications, such as touch detection, sag of bridges, spine curvature, and/or the like. In non-limiting embodiments, these considerations may be realized by using higher-order Bézier curves. Such curves may be used to represent the shape of a 1-D surface (such as a string of RF transponders) or a 2-D surface.

In non-limiting embodiments, an nth-order Bézier curve in 2-D space for a 1-D array of RF transponders that can deform to various shapes in 2-D space is represented as the following formula:

$$S(p = \{C_i\}, t) = \sum_{i=0}^{n} \binom{n}{i}(1-t)^{n-1}(t)^i C_i$$

where $0 \leq t \leq 1$ and $C_i$ are the n+1 control points which define the set of parameters p that define the curve. A Bézier curve will always start with the first control point and end with the last control point, while the remaining control points define the tangents of the curve.

Figure 4A:
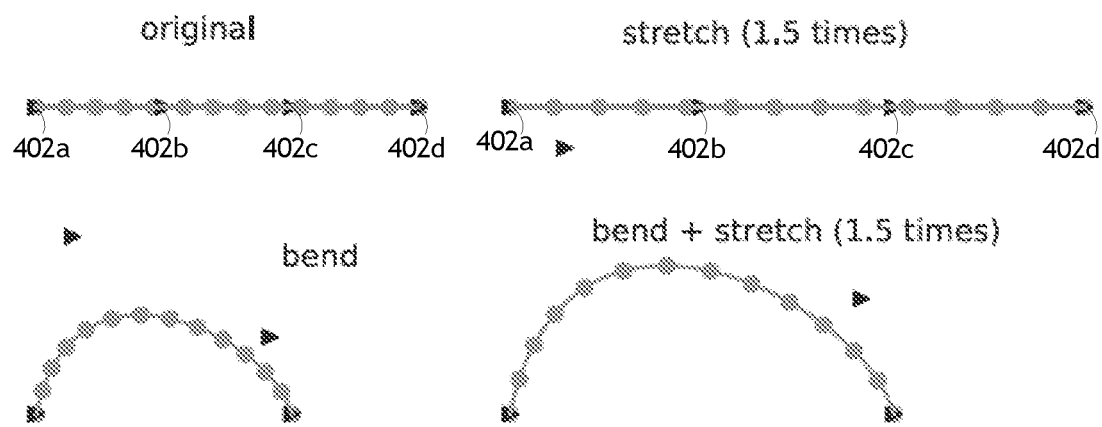
FIGS. 4A and 4B show Bézier curves and surfaces usable with non-limiting embodiments of a system and method for tracking shapes.
Figure 4B:
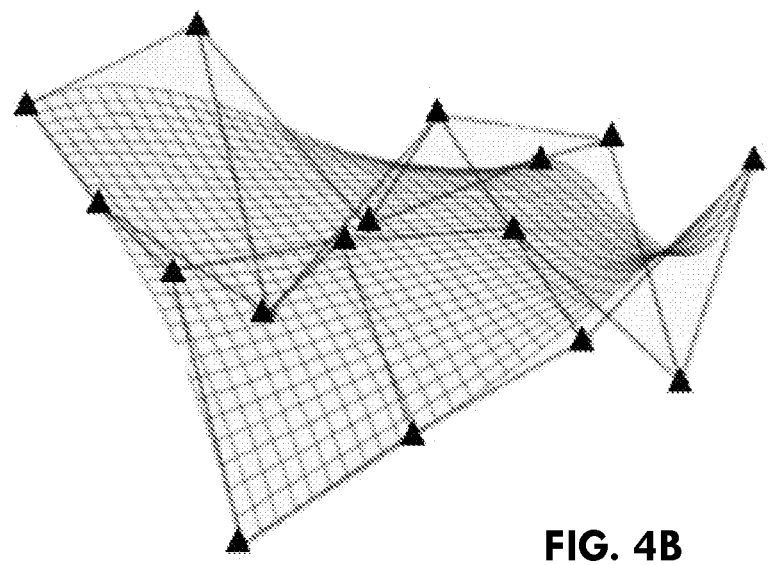

FIGS. 4A and 4B show Bézier curves and surfaces with control points represented by triangles that may be used in non-limiting embodiments to represent the shape of a surface. FIG. 4A shows a cubic (3rd order) Bézier curve that may be used to characterize many curves on the human body (e.g. spine, stomach, etc.) as well as many everyday surfaces (e.g. carpets, bridges, buildings, etc.) while minimizing over-fitting. The system may utilize four 2-D control points 402a-402d to represent the relative shape of an arbitrary string segment $C_0(x_0=0, y_0=0)$, $C_1(x_1, C_2(x_2, y_2), C_3(x_3, y_3=0)$, resulting in 5 unknown variables. The first control point may be set to the origin and the final control point may be constrained to lie on the x-axis because only the shape of the surface (e.g., relative coordinates of the control points) is being determined and not the location of the surface in 3-D space.

Referring to FIG. 4B, in non-limiting embodiments a 2-D surface may be modeled using Bézier surfaces based on a Bézier curve in 3-D space. FIG. 4B shows a representation of Bézier surfaces according to non-limiting embodiments. A general cubic Bézier surface is constructed as the tensor product of two Bézier curves as defined by the following formula:

$$S(p = C_{ij}, u, v) = \sum_{i=0}^{n}\sum_{j=0}^{m} B_i^n(u) B_j^m(v) C_{ij},$$

where each underlying curve is given by the following formula:

$$B_i^n(u) = \binom{n}{i}(1-u)^{n-i}(u)^i,$$

While the above formulas model complex surfaces due to the large number of control points, in non-limiting embodiments fewer control points are sufficient over small surface areas. The above formulas may therefore be simplified by using two curves that are univariate blending functions, where the variables u and v are two orthogonal parametric directions. In this formulation, the surface is controlled by two orthogonal curves, each traversing along two orthogonal axes. The control points Cij in a tensor-product surface are organized topologically into a rectangular array, and the blending functions corresponding to the control points are shown in the following formula:

$$S(p=\{C_i,C_j\},u,v)=B_i(u)B_j(v)C_iC_j$$

In non-limiting embodiments, larger shapes formed by structures such as buildings or bridges may not be fully modeled using a cubic Bézier surface. Instead of employing higher-order curves to address these scenarios, which may lead to over-fitting, a large number of control points may be introduced in specific parts of the surface. The surface may be partitioned into smaller segments with overlaps, each of which may be modeled as a separate cubic Bézier surface. The extremities of these segments may be stitched together to recover the shape of the entire surface using the following process that assumes continuity and differentiability of the surface it models: (1) intersecting any two surfaces at the RF transponder(s) common to them (e.g., at their extremities); and (2) rotating the second surface so that the normal vectors to the tangent of the surfaces at the intersecting RF transponder(s) align. By partitioning surfaces into separate segments in this manner, control points are distributed evenly across the entire surface.

While Bézier curves are an effective formulation to represent a large variety of surfaces, not all of them may obey the constraints of the material that the surface is made of. In non-limiting embodiments, constraining parameters may include maximum curvature and stretch. For example, surface models for fabrics may be used to measure the amount of energy required to deform the shape into any curve, depending on constraints of stiffness and elasticity that the material is associated with. Any surface model candidates in a particular generation having a required energy that exceeds a threshold may be eliminated from each generation of Bézier surfaces in the genetic natural selection algorithm. In this manner, outliers may be removed whose shapes are unlikely to form in the real-world due to material constraints.

Non-limiting embodiments may constrain the surface parameters by stretch by measuring the energy expended to deform the surface into a specific length. The net displacement of each RF transponder from each other, relative to their prior configuration at the time the RF transponders were attached to the surface, is represented in the following formula:

$$E_{elastic} = \sum_{i=0}^{n-1} |d_i - D|$$

where D is the prior known spacing between transponders and $d_i$ is the surface distance between tag i and i+1.

In non-limiting embodiments, the energy required to bend the surface into a specific curvature, starting from an initially planar surface, may be determined by the computing device. Such a determination may be based on a fast energy-based surface wrinkle model to calculate the surface smoothness. Mathematically, the curvature of the Bézier surface is determined by computing the angular rotation between control points. Specifically, $\theta_j$ is the angle formed by the segments connecting control points $C_{j-1}$, $C_j$, and $C_{j+1}$, such that the computing device may then determine the result of the following formulas:

$$E_{stiff} = \sum_{i}^{n-1} E(C_i)$$

-continued $$\text{where } E(C_i) = \sum_{i-1}^{i+1}(e^{-\theta j} - e^{-\pi})$$

Existing surface models may be used to compute the total energy required to distort the surface into a given geometry specified by the Bézier surface parameters in the following formula:

$$E_{total} = k_e E_{elastic} + k_s E_{stiff} + k_g E_{gravity}$$

In the above formula, $k_e$, $k_s$, $k_g$ represent elasticity, bending, and density constraining parameters, respectively. For each surface parameter in any given generation of surfaces in the genetic algorithm, the above energy ($E_{total}$) is computed and any surfaces whose total required energy exceeds a threshold are eliminated, thereby rejecting any outlying, unrealistic surface geometries that the computing device may output.

With continued reference to FIG. 3, at step 306 an estimated position of where each RF transponder would be located on each surface model is determined. The estimated position may be determined based on the surface model and a predetermined spatial arrangement of the plurality of RF transponders on a surface having a known shape (e.g., planar, flat, straight, default, etc.). For example, given a Bézier surface with constraints on curvature and elasticity, the coordinates of the RF transponders on the surface may be determined based on a projection. In non-limiting embodiments, the RF transponders are arranged in a rectangular array at a predetermined distance D from each other when the surface is in a predetermined position. For any Bézier curve that the surface deforms to, a geometric projection of the positions of the RF transponders is projected from its initial configuration (e.g., a planar arrangement) to that of the new shape. This accounts for both the curvature of the Bézier surface as well as the stretch that the surface experiences uniformly.

Referring again to FIG. 3, at step 308, radio environment parameters are determined for each surface model generated at step 304. The signals received by the reader device from the RF transponders may be affected by radio environment parameters. Thus, for each shape of the generation, radio environment parameters are determined. Such a determination may be based on the surface model and the locations of RF transponders on them. The radio environment parameters that best-fit the observed signals (e.g., the observed channels) are determined for each surface model using the following formula:

$$E^* = \arg\min_E \sum \|h_{est}(S(p), E) - h_{obs}\|^2$$

In the above formula, $h_{est}$ is the estimated radio environment parameters for the surface model $S(p)$ and $h_{obs}$ is the observed radio environment parameters determined from signals received from the RF transponders at step 302.

In non-limiting embodiments, the radio environment parameters may include the following components that influence the wireless channels as the response signals traverse from the RF transponders to the reader device: (1) phase shifts at the RF transponder that may be produced, for example, by change in orientation of the RF transponder that causes shifts in the phase of signals observed from it; (2) signal multipath as a result of the multiple paths a wireless signal from the RF transponder traverses as it reflects off walls, furniture, objects, people, and/or the like; and (3) phase shifts at the reader device that may be arbitrarily introduced by the radio frontend of the reader device to signals received across different RF transponders.

The orientation of an RF transponder may not affect the phase of the response signals it reflects if the RF transponders were perfectly omnidirectional point-objects. However, RF transponders do not include specific beam patterns and their orientations in 3-D space can alter the observed phase value at the reader device. Accordingly, phase offsets due to the orientation of each RF transponder is an additional variable that can be inferred as part of the radio environment parameters. In order to directly estimate the phase offset per RF transponder by modeling phase shift from the RF transponder orientation, the placement of the RF transponders is predetermined. For example, with planar RF transponders, the orientation of each transponder may be orthogonal to the tangential plane to the surface at the location of the transponder. An ambiguity of whether each transponder is facing up or down (e.g., is turned upside down) can be eliminated during the time the RF transponders are arranged on the surface by ensuring that all transponders are oriented along the same direction initially (e.g., all face-up or face-down) to avoid measurement errors. Further, RF transponders of the same make and manufacture may be used as such a set of transponders are likely to have predictable phase shifts based on changes in orientation.

Figure 5:
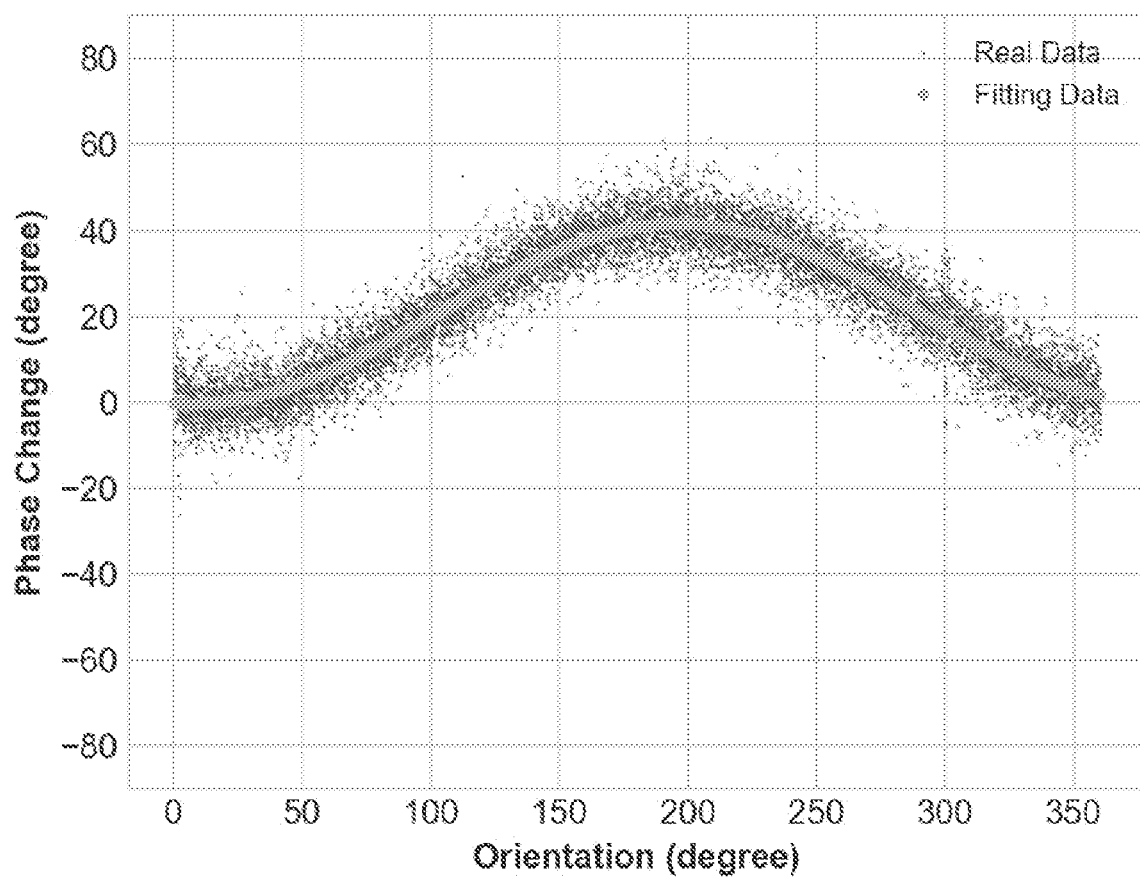
FIG. 5 shows test data for observed phase measurements according to a non-limiting embodiment of a system and method for tracking shapes.

Referring now to FIG. 5, a scatter-plot is shown of the observed phase measurements in a non-limiting implementation in which thirty Omni ID IQ-150 RF transponders were measured across orientation. As shown, the relationship between phase shift and orientation is predictable (subject to noise) introducing a small mean error of 10 degrees. Therefore, in non-limiting embodiments the system may calibrate and compensate for the phase shift introduced by a RF transponder solely based on its orientation. Phase offsets from the orientation of RF transponders can be corrected for without introducing additional variables to estimate in its optimization.

Figure 6:
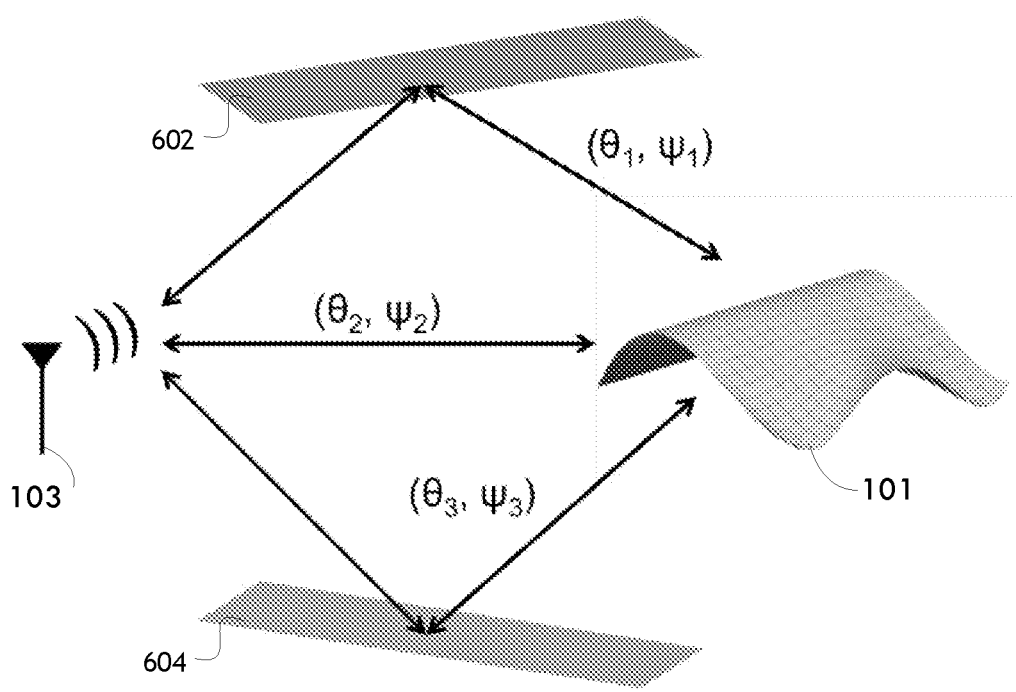
FIG. 6 shows signals traversing along multiple paths from RF transponders to a reader device according to non-limiting embodiments of a system and method for tracking shapes.

Referring now to FIG. 6, multiple signal paths are shown between RF transponders on a surface 101 and an antenna 103 of a reader device according to non-limiting embodiments of a system and method for tracking shapes. As shown, some paths involve reflecting off of surfaces 602, 604. The multiple paths represented are: $(\theta_1, \psi_1)$, $(\theta_2, \psi_2)$, $(\theta_3, \psi_3)$. The attenuations and phase shifts experienced by a signal along different paths the signal traverses, e.g., as a signal reflects off various objects 602, 604 in the environment between each transponder and antenna, may be estimated. Estimating each of these quantities independently per transponder may be infeasible, given that only one phase measurement per transponder may be used. Accordingly, in non-limiting embodiments the algorithm accounts for the fact that adjacent RF transponders will experience similar multipath characteristics due to their proximity. In such non-limiting embodiments, the RF transponders on the surface are treated as an array of antennas. The computing device may then apply antenna array algorithms to process the known wireless channels at the array of transponders as well as their known geometric configurations, as previously determined, to separate the various signal paths.

Figure 7:
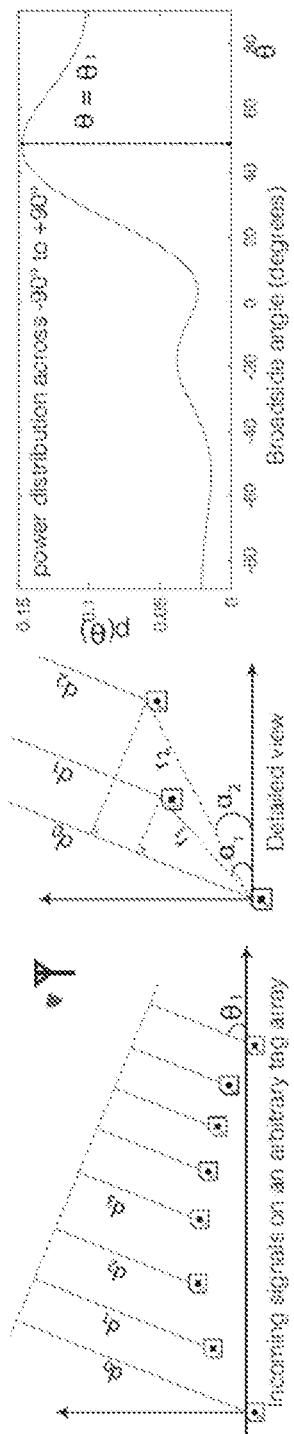
FIG. 7 shows an implementation of the MUSIC algorithm according to non-limiting embodiments of a system and method for tracking shapes.

Non-limiting embodiments may utilize the Multiple Signal Classification (MUSIC) algorithm to perform antenna array processing. However, unlike many antenna arrays that form regular shapes (e.g., linear, circular, rectangular, etc.), in non-limiting embodiments the RF transponders may be distorted into arbitrary shapes whose candidate set of surface models have already been determined. As a result, for each surface model candidate in a generation, the MUSIC algorithm may be extended to operate under arbitrary array configurations to estimate the angle-of-arrival $\theta_1$ from a single-antenna reader device to the transponders. The transponders are at a known but arbitrary geometry with polar coordinates $(r_i, \alpha_i)$ as shown in FIG. 7. The MUSIC algorithm plots the power of the signal $P(\theta)$ received along each direction $\theta$ with a peak(s) at the true direction(s)-of-arrival (e.g., $\theta_1$), also as depicted in FIG. 7.

The power of the received response signal from any spatial azimuthal angle $\theta$ and polar angle $\psi$ is represented by the following formula:

$$P(\theta, \psi) = \frac{1}{|a(\theta, \psi)^\dagger E_n E_n^\dagger a(\theta, \psi)|} \quad (11)$$

$$\text{where: } a(\theta, \psi) = [e^{4\pi j r_i \cos(\theta - \alpha_4)\cos(\psi - \beta_4)/\lambda}]_{i=1,\ldots,N}$$

where $(r_i, \alpha_i, \beta_i)$ are the polar coordinates of the RF transponders, $\lambda$ is the signal wavelength, j is the square root of $-1$, $E_n$ are the noise eigenvectors of $h_{obs} h^\dagger_{obs}$, $h_{obs}$ represents the vector of observed wireless channels across the RF transponders (e.g., at step 302 of FIG. 3) and $(\cdot)^\dagger$ is the conjugate-transpose operator. The computing device then estimates the locations of local maxima (peaks) of P ($\theta$, $\psi$) to obtain the azimuthal and polar directions-of-arrival: $\{(\theta_k, \psi_k), k=1, \ldots, p\}$ of the p signal paths. At this point, the computing device can obtain the magnitude and phase of the signals corresponding to each path by solving the following optimization provided by the following formula:

$$\min_{a_1, \phi_i, \forall k} \sum_{k=1}^{p} \left\| h_{obs} - a_i e^{-j\frac{\phi_k + 4\pi j r \cos(\alpha - \beta_k)\cos(\beta - \psi_k)}{\lambda}} \right\|^2$$

The above optimization formula is a least-squares optimization and can be solved in polynomial-time. The computing device applies the least-squares method to obtain, for each signal path k, the attenuation $a_k$ and phase shift $\varphi_k$ experienced by the signal.

In non-limiting embodiments, the computing device accounts for phase shifts introduced by the RF chains (e.g., an arrangement of transmitters, receivers, cables, amplifiers, instruments, and/or other like components) of the reader device. Because non-limiting embodiments of a system for tracking a shape may be implemented with a single-antenna reader device, only one unique phase shift may be introduced across all RF transponders. Accordingly, one unknown phase value is effectively applied across all RF transponders and across all of the signal paths each transponder experiences. This phase shift is captured as an offset to the term $\varphi_i$, obtained from the above optimization formula, and therefore may already be determined. The value $\varphi_i$ represents both the phase shift introduced by path i as well as the reader device.

Referring again to FIG. 3, at step 310 one or more surface models are selected from the first plurality of surface models as a best-fit for the current unknown shape of the surface being tracked based on the observed signals from the RF transponders. In non-limiting embodiments, the selection may be the first selection of a plurality of iterative selections in a genetic natural selection algorithm to optimize for the best candidate surface model. At step 312 it is determined whether the selected surface model is a sufficient best-fit (e.g., within a threshold distance). In non-limiting embodiments the first iteration of surfaces may not be a sufficient best-fit and, as a result, the method may proceed to step 304 to generate a next generation of surface models. Based on the observed channels from each transponder ($h_{obs}$) and the estimated channels based on the geometry of the surface model S(p), the following formula may be used to find the surface parameters p that best fit:

$$p^* = \arg\min_p \min_E \sum \|h_{est}(S(p), E) - h_{obs}\|^2$$

At step 310 of FIG. 3, surface models are eliminated from the first plurality of surface models that poorly fit the observed signals. A goodness-of-fit metric may be generated in non-limiting embodiments based on the observed channels, the surface parameters of each surface model, and the radio environment parameters for each surface model determined at step 308. A surface model S having RF transponders positioned at polar coordinates may be represented as n dimensional vectors: $(r, \alpha, \beta)$. In this example, $h_{obs}$ denotes the vector of n wireless channels obtained from these transponders. In addition, the azimuthal and polar directions-of-arrival of the signal from the reader device are represented as: $\{(\theta_i, \psi_i), i=1, \ldots, p\}$ for the p signal paths. The values $(a_i, \varphi_i)$ denote the attenuation and phase shift experienced by the signal for each of these paths, as described herein. The goodness-of-fit of the candidate shape S may be represented as follows:

$$g(S) = 1 \Big/ \sum_{k=1}^{p} \left\| h_{obs} - \alpha_i e^{-j\frac{\phi_k + 4\pi j r \cos(\alpha - \beta_k)\cos(\beta - \psi_k)}{\lambda}} \right\|^2$$

The computing device then selects the top $\sigma$ fraction (e.g., $\sigma=20\%$ in a non-limiting example) of the surface models based on their goodness-of-fit to pass to the next generation. Because the optimization culls $(1-\sigma)$ fraction of the individual surface models at any given point in time, over time the genetic algorithm converges in a finite number of steps $$\left(O\left(\log_{\frac{1}{1-\sigma}} N\right)\right)$$

steps), where N is the number of initial surface models in the first generation (e.g., the first plurality of surface models) generated during the first iteration of step 304. In a non-limiting example, the algorithm converges in approximately 20 iterations from a randomly chosen seed. It will be appreciated that numerous variations are possible depending on the availability of computing resources, the size and complexity of the surface models, the number of RF transponders, and/or other like considerations, and that any number of iterations may be implemented. The natural selection algorithm favors individual surface models that fit the observed channels, thereby resulting in progressive improvements in the goodness-of-fit metric with each iteration. In testing of non-limiting embodiments, results achieved sub-centimeter errors in displacement of surfaces measuring 40 cm per-side in 80% of tests. The test data for such non-limiting embodiments is shown in FIG. 8D.

At step 312 of FIG. 3 it may be determined that the goodness-of-fit metric of one or more surface models in the current generation (e.g., iteration) is sufficient. For example, the goodness-of-fit metric may be determined to be a best-fit at step 312 if it satisfies a threshold distance. The method may then proceed to step 314 and the shape of the surface at the time the response signals were received from the RF transponders may be determined and output based on the one or more best-fitting surface models. In non-limiting embodiments the first generation of surface models may not be a sufficient best-fit and, as a result, the method may proceed to step 304 to generate a next generation of surface models as part of the genetic natural selection algorithm. However, it will be appreciated that in some non-limiting embodiments only one iteration may be used.

In non-limiting embodiments, for each shape in the generation, a goodness-of-fit metric is determined to identify which shapes (surface models) to pass on to the next generation. For example, referring to FIG. 3, the one or more surface models identified at step 310 may be passed to step 316 after step 312. At step 316, the one or more selected surface models are processed according to cross-over and/or mutation operations to influence the next generation of surface models generated at step 304. A cross-over operation combines two or more surface models to result in a hybrid surface model (e.g., hybrid shape). A cross-over operation may amplify positive characteristics and focus on fine-grained solutions to the goodness-of-fit metric. Because the surface parameters of each surface model may be represented as a set of control points, the computing device may perform a cross-over operation of two surface models by averaging the corresponding control point coordinates for the surface models. The resulting surface model is a hybrid shape that inherits features from both of the surface models. A mutation operation randomly alters the surface parameters of the surface models, within constraints based on the previously selected surface models. A mutation operation facilitates the computing system to avoid local optima. The computing device may introduce a random off-set to one of the control points in one or more selected surface models. The off-set may be from a Gaussian distribution with a standard deviation of D, which is the mean displacement between the RF transponders.

It will be appreciated that non-limiting embodiments may use other approaches, rather than a generic natural selection algorithm, to reconstruct a shape from the radio signals received from the RF transponders (e.g., phase and signal strength readings). For example, a Monte Carlo search method, deep learning (e.g., deep q-learning or other techniques), and/or other techniques may be utilized to determine different RF transponder arrangements to generate a specific pattern of backscatter signals.

In non-limiting examples, RF transponders may be chosen or designed based on how well the RF transponders interact with the human body and/or how minimally the phase of signals outputted by the RF transponders changes across different orientations. For example, RF transponders that perform consistently while both attached to a body and detached from a body may help reduce the amount of attenuation caused by the human body. Further, RF transponders may be chosen or designed based on radio sensitivity and/or directivity. RF transponders having a relatively weaker directivity may be desirable because a strong directivity may require the RF transponders to directly face the reader device. RF transponders may also be chosen or designed to be as small, thin, and flexible as possible, allowing for the RF transponders to be integrated into materials, such as garments, in a non-intrusive and non-restrictive manner. In non-limiting embodiments, the RF transponders may be Omni-ID IQ 150 RF transponders manufactured and sold by Omni-ID, Inc. These example RF transponders are 1.2×5.2 cm, light-weight, thin, and have consistent performance on and off a body. It will be appreciated that various types of RF transponders may be used.

The reader device 100 may be any suitable device having an antenna or in communication with an antenna and configured to communicate one or more activation signals and receive a plurality of response signals from the RF transponders 102a-h. In non-limiting embodiments, the reader device may be an Impinj Speedway RFID reader equipped with a single Ettus VERT900 antenna, which provides a software interface for wireless channels. Although the Impinj Speedway RFID reader and other reader devices support multiple antennas, implementations of the system may involve disabling and/or not using all but one antenna. It will be appreciated that various types and implementations of reader devices may be used. In non-limiting embodiments, a single antenna may be used to reduce the cost of hardware and the amount of effort required to calibrate the antenna and reader device. To comply with regulations (e.g., FCC regulations in the United States), reader devices may be configured to "frequency hop" across 50 channels from 902 MHz to 928 MHz at an interval of approximately 0.2 seconds. Once the RF transponders are in an operational range of the reader device 100, the reader device 100 may generate an observation data stream that contains all the low-level wireless channel data, including a Universally Unique Identifier (UUID), phase, signal strength, frequency, and/or the like.

In non-limiting embodiments, the reader device or a separate computing device may track a shape in real-time or near-real-time. For example, the reader device or a computing device may use a sliding window technique to extract quasi-simultaneous readings for different RF transponders from a data stream of received response signals. The reader device extracts the response signals of the same frequency from the data stream. The readings of each RF transponder occurs in a short time period (e.g., 0.1 seconds) such that, when the time period expires, the data is processed. Some of the RF transponders may not communicate back to the reader device due to potential body or object occlusion. However, in such instances, the set of incomplete data may still be processed even though accuracy errors may have been introduced during the collection process. For example, measurements may be inputted to a process or function that generates an estimate of a value based on a series of sequential measurements such as, but not limited to, a Kalman filter. A sliding window process may generate numerous independent array readings (e.g., 30) per second.

Non-limiting implementations of a system for tracking a shape were tested with various surface materials. For a paper surface, RF transponders were attached to a 7 cm×40 cm paper frame to evaluate performance in various multipath-rich settings. For other tests, RF transponders were attached to 0.5 mm thick latex sheets (one 3 cm×15 cm and the other 30 cm×40 cm) to evaluate system performance under stretch and curvature. A 3 mm thick cotton fabric was used for another test to evaluate performance with day-to-day clothing. Further tests were performed on woven conductive fabrics to verify if the system operates on conductive soft surfaces that may be generally used to shield external electromagnetic signals.

For the tests, a non-limiting implementation of the system was evaluated in a variety of multipath rich settings in an 8.5 m×2 m indoor space with the RF transponder(s) and reader device separated by up to 3 m. To characterize performance of the system, the absolute error in the position of RF transponders, measured in mm on the surface of the material, was used as a performance metric. To obtain ground-truth transponder positions, a camera-based fiducial tracking system was implemented using ARToolKit and fiducial markers were affixed to the surfaces. The ARToolkit calibration program indicates a sub-millimeter baseline accuracy. Based on the fiducial marker tracking results, a surface interpolation was performed to reconstruct the surface's shape and identify ground truth positions for the RF transponders.

In non-limiting embodiments, a number of RF transponders is chosen for a surface based on various considerations including, for example, accuracy, inter-transponder signal coupling, processing requirements, type of material, size of surface, and/or the like. Although an increased number of transponders provides more measurements to use in the calculations, closely proximate transponders may cause inter-transponder signal coupling. To test considerations for RF transponder spacing, three surfaces were created by placing a 1-D array of RF transponders (Omni ID 150 tags) on flexible paper platforms. All the prototypes were of the same total length (40 cm) but with a different transponder spacing (2 cm, 3 cm, 4 cm), resulting 18, 13, 10 transponders respectively. For each surface tested, three classes of shapes were examined: concave, convex, and wave-like. To avoid error due to movement of the fiducial markers, it was ensured that the setup was static when collecting the ground truth data. During the evaluation, the experimenter moved around the prototype in front of the antenna of the reader device (approximately 0.5-1 meter away), while the reader device and antenna were placed on the floor. The process was repeated three times and wireless channel data was collected for each shape. For each shape sensing experiment, at least 500 independent snapshots of channel data were obtained with an average refresh rate of approximately 16 Hz.

Figure 8A:
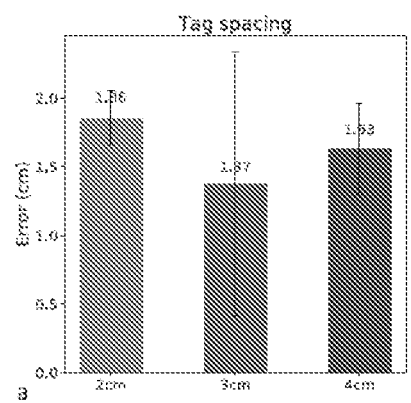
FIG. 8 shows test data for various surface materials using a non-limiting embodiment of a system for tracking shapes.
Figure 8B:
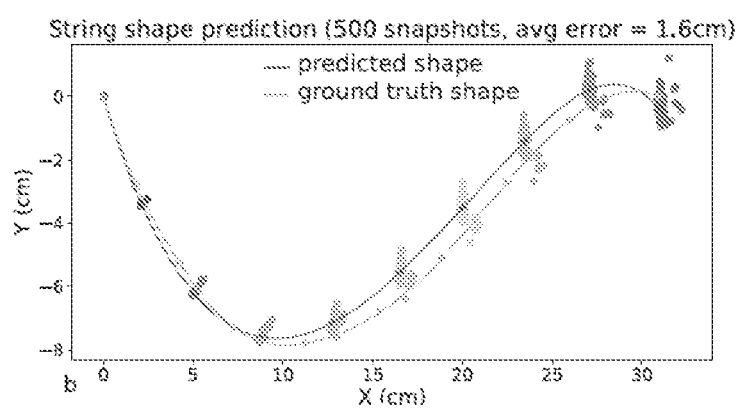
Figure 8C:
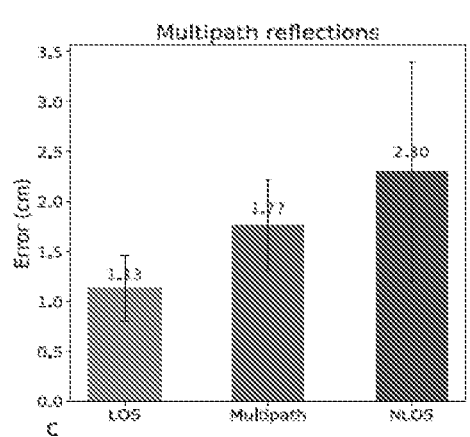
Figure 8D:
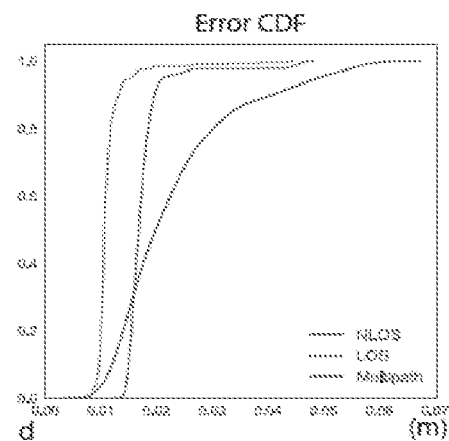

Referring now to FIGS. 8A-D, testing data is shown for the above-described tests. As shown in FIG. 8A, all three configurations resulted in an average error between 1.3 and 1.9 cm. Among the various configurations, the spacing of 3 cm resulted in a slightly higher accuracy. However, the remaining configurations only experienced a minor reduction in accuracy relative to this configuration. Based on the tested transponder positions, a spacing of 4 cm with 10 transponders on the string was found to be sufficient to compute the unknown variables that characterize the shape of each surface.

In non-limiting embodiments, the multiple paths of the response signals from the RF transponders to the reader device (based on the signals reflecting off of walls, objects, and bodies) may be disambiguated. To evaluate the effect of multiple signal paths, tests were performed on non-limiting embodiments of a system for tracking shapes. The environments in which the tests were conducted are categorized as three groups: direct line-of-sight (e.g., with minimal obstructions in the environment), multipath-rich settings (e.g., with presence of large metallic and other reflectors in the environment), and non-line-of-sight (e.g., RF signals traverse only through reflected paths to the tags). A 1-D string of RF transponders with a spacing of 3 cm was used for the test. For each multipath configuration, two classes of shapes (concave and wave) were tested. FIGS. 8C and 8D depict the error in transponder position across the different multipath environments. A mean error of 1.13 cm, 1.77 cm, and 2.30 cm was observed across the three classes of environments: line-of-sight, multipath, and non-line-of-sight, respectively. While the accuracy diminished by a measurable amount in the absence of direct signal paths, the tested non-limiting implementation remained largely robust to the multipath environments due to the algorithms described herein.

Tests were also performed on the effect of material flexibility. In particular, non-limiting implementations of a system for tracking a shape were tested under two different types of stress related to flexibility: stretch and bend. Four objects were created to accommodate stretch and bend using different types of materials: a latex rubber string (30 cm), a latex rubber surface (20 cm×20 cm), a cotton string (30 cm), and a cotton surface (30 cm×40 cm). To evaluate stretch only, the objects were hung on a wood frame vertically and different weights (0.5 kg and 1 kg) were hooked to the bottom of the material. Due to gravity, the shapes stretched differently. To test the stretch and the bend at the same time, the objects were stretched and placed horizontally on a frame and weights were attached. Convex, concave, and wave shapes were tested in each configuration. The shape deformation ground truth was captured by the fiducial tracking system in real-time to capture changes in shape over time.

Figure 9:
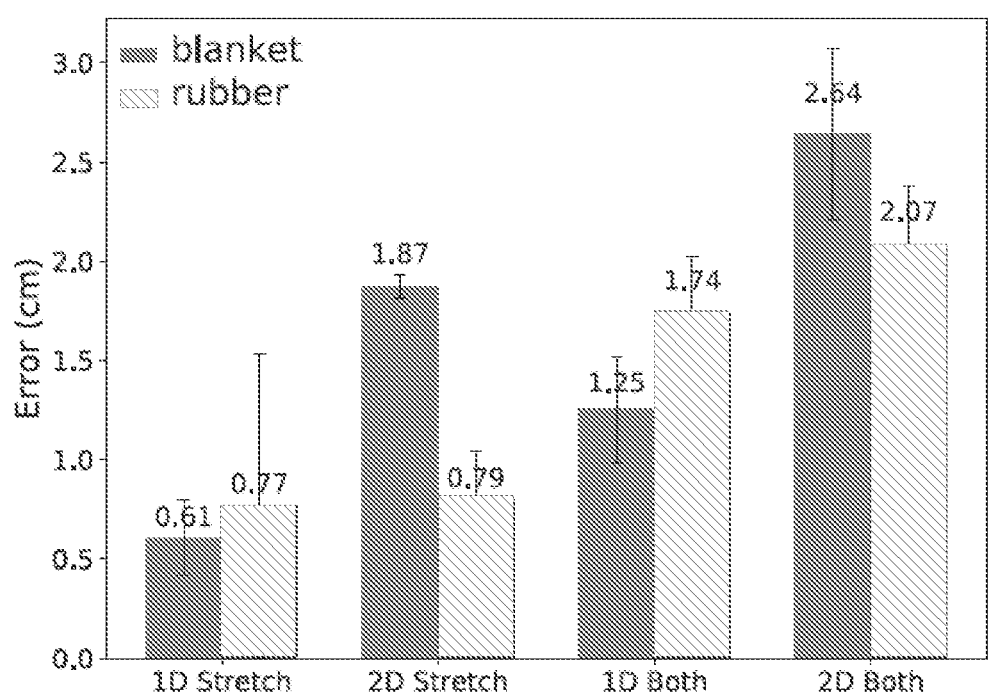
FIG. 9 shows test data for material flexibility using a non-limiting embodiment of a system for tracking shapes.

FIG. 9 shows results for different types of material according to the above-described tests. An error between 0.5 cm and 2.6 cm is observed across different materials and different deformations, indicating that the system is operable across various types of materials despite the presence or absence of stretch. Among the different scenarios, the accuracy under both stretch and bend is less than the accuracy under only stretch, primarily due to the more complex shapes that result from both deformations. More iterations may be necessary to converge such complex shapes in the natural selection algorithm described herein to optimize the goodness-of-fit metric.

The following table (Table 1) shows an overview of the absolute mean errors in different configurations:

TABLE 1

|  | Bend | Stretch | Both |
| --- | --- | --- | --- |
| String | 13 mm | 5.3 mm | 17 mm |
| Surface | 19 mm | 8.7 mm | 24 mm |

As shown, the non-limiting implementations tested are able to determine the transponder positions at a sub-centimeter accuracy and determine a fine-grained shape at 1 cm for a 0.4 m string and 2 cm for a 0.3×0.4 m surface.

Figure 10A:
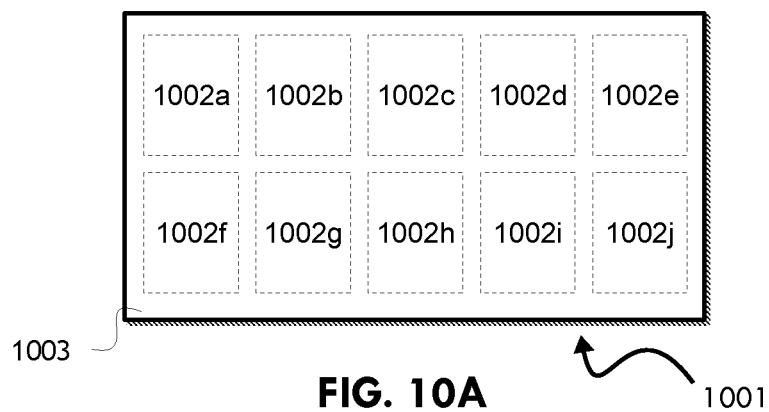
FIGS. 10A and 10B show a surface for tracking user interactions according to a non-limiting embodiment.
Figure 10B:
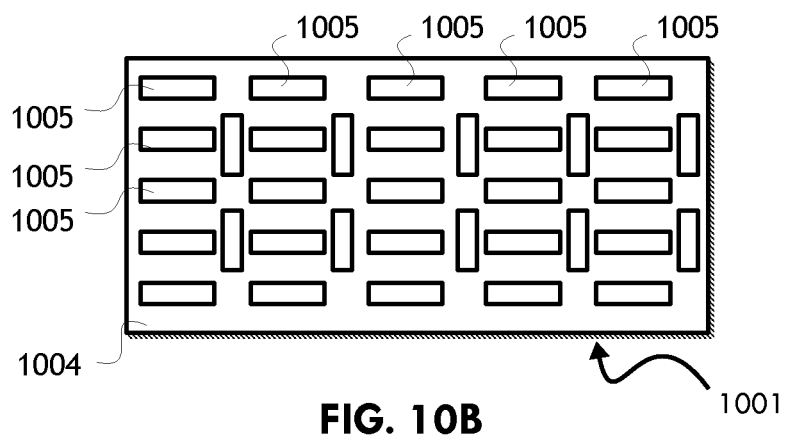

In non-limiting embodiments, the surface may be a 3-D depressible (e.g., soft) touch screen or interactive surface. Referring to FIGS. 10A and 10B, an interactive surface 1001 is shown having a front side 1003 and a back side 1004. By determining the shape of the surface 1001 based on the deformation that results from a user interacting with a surface, the location and pressure of the user's interaction can be determined. The front side 1003 shows the surface 1001 divided into ten regions 1002a-j for differentiating interactions. The back side 1004 shows 35 RF transponders 1005 arranged over the surface. As an example, a user may place his or her hand on the front side 1003 of the surface 1001, depressing a region of the surface overlapping region 1002g. A single detected depression (e.g., change in shape)

may be used to determine which region 1002g the user touched and with what force (e.g., based on the depth of the depression). It will be appreciated that any number of regions may be utilized.

Figure 11:
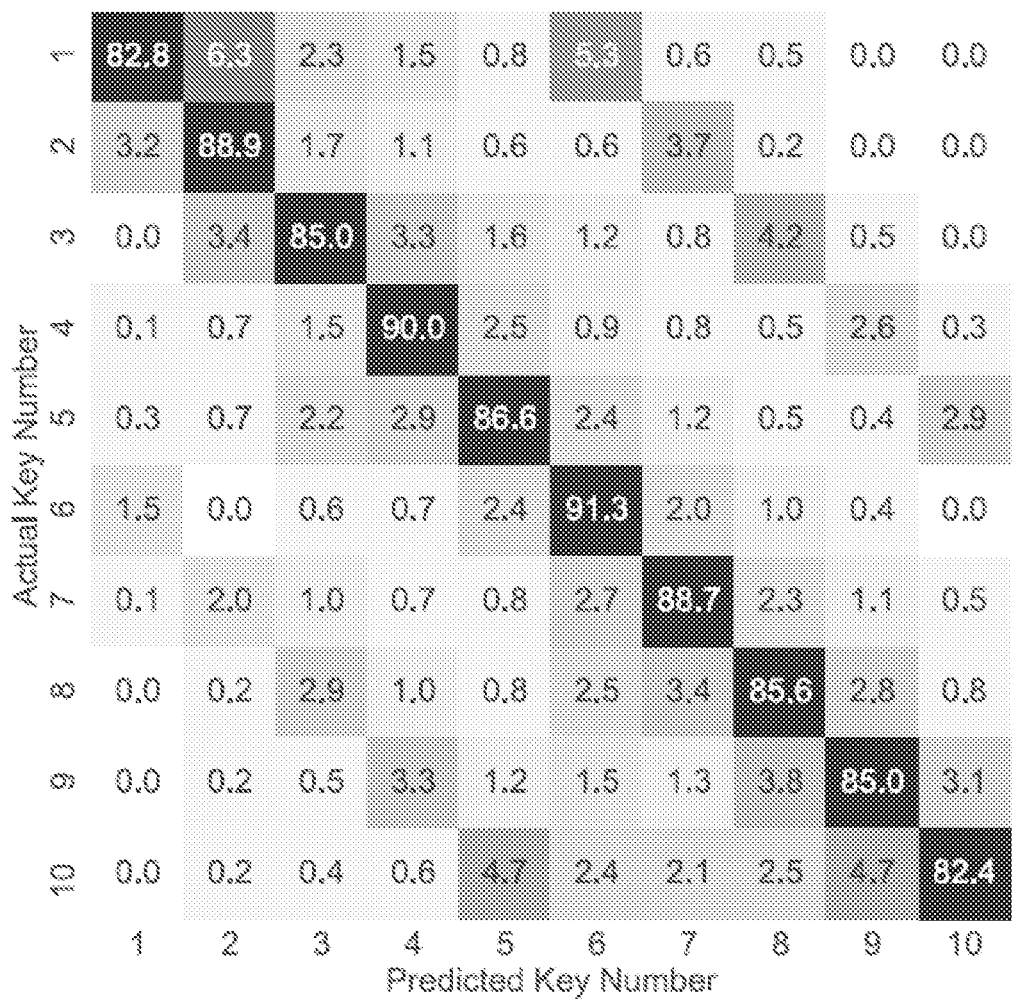
FIG. 11 shows test data for the non-limiting embodiment shown in FIGS. 10A and 10B.

Referring now to FIG. 11, a confusion matrix is shown from touch-based experiments performed on the front side 1003 of the surface 1001 shown in FIG. 10A. The confusion matrix shows that 500 touch-point samples were measured with a 87.3% mean accuracy.

In non-limiting embodiments, the system for tracking a shape may be used to track the curvature of a spine (e.g., a posture). In such implementations, a user may wear clothing with RF transponders aligned on the user's back. A reader device may be mobile and carried with the user. For example, a 1-D array of RF transponders having 4 cm spacing between each transponder may be positioned along a person's spine to measure the person's posture. In tests, an ARToolkit camera-based system was used to develop a baseline. Tests showed a mean error of 17 mm in the positions of the RF transponders.

Figure 12:
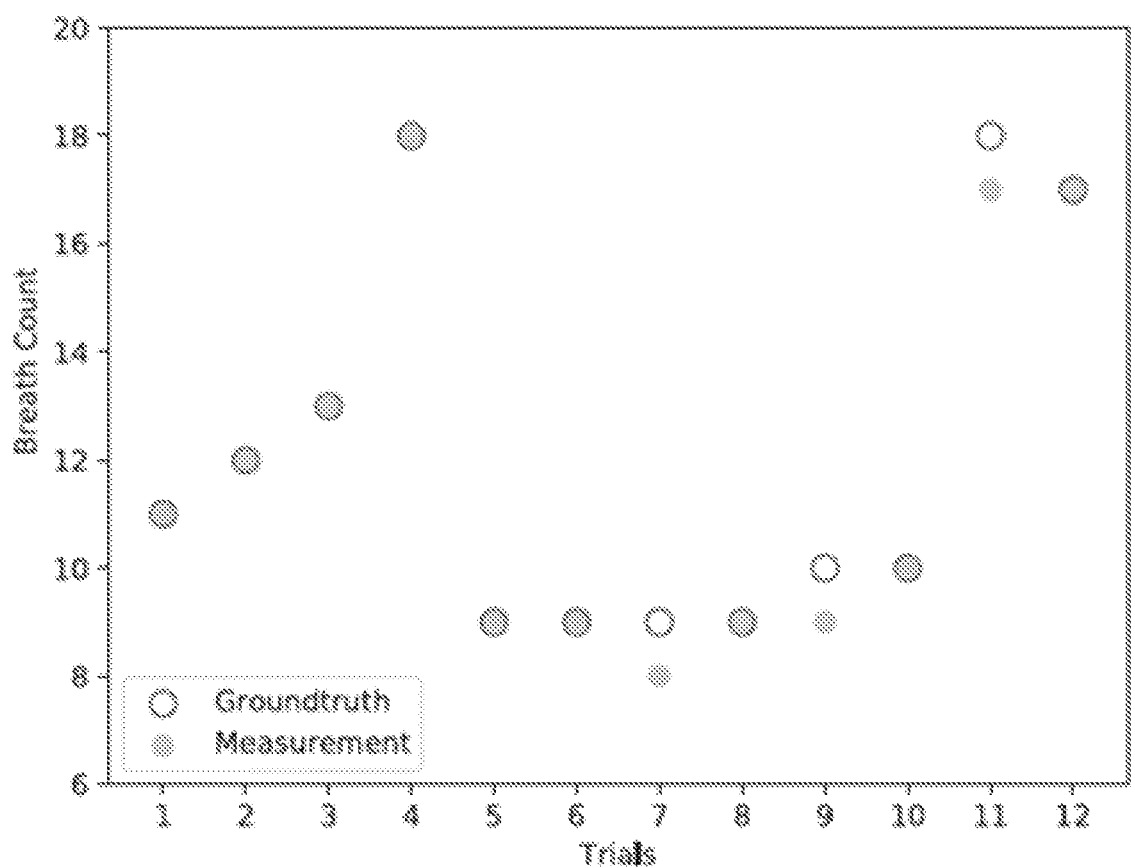
FIG. 12 shows test data for measuring a user's breathing according to a non-limiting embodiment.

In non-limiting embodiments, the system for tracking a shape may be used to track a user's breathing. For example, a 1-D array of RF transponders may be arranged along a user's chest. A user may then self-report a breathing rate for a predetermined time period (e.g., 30 seconds) for a predetermined number of times (e.g., 12) after different activities of different intensities. FIG. 12 shows test results from tests performed with a non-limiting implementation of tracking a user's breathing in which a 95% accuracy was observed.

In non-limiting embodiments, the system for tracking a shape may be used to track a shape of a floor surface (e.g., wood, carpet, mat) and/or furniture (e.g., a chair, couch, mattress, etc.). Such applications may be used to determine the presence, location, and impact (e.g., weight, speed, etc.) of one or more objects or persons. In non-limiting embodiments, the system for tracking a shape may be used to track a shape of architectural structures, such as bridges, roads, buildings, and/or the like. Such applications may be used to determine the sag, vibration, stress, load, and/or other like features of a structure. It will be further appreciated that non-limiting embodiments of a system for tracking shapes may be used in various other contexts and applications where it is desirable to track the shape of any object or person over any period of time.

In non-limiting embodiments, the system for tracking a shape may be combined with a system for tracking body movement. For example, the non-limiting embodiments described herein may be used in combination with the systems and methods described in International Patent Application No. PCT/US18/64470, titled System and Method for Tracking a Body and filed on Dec. 7, 2018, the entirety of which is hereby incorporated by reference.

Although non-limiting embodiments have been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method for tracking a shape of a surface, the surface comprising a plurality of radio frequency (RF) transponders arranged thereon, the method comprising:
generating, with at least one processor, a first plurality of surface models based on the surface, each surface model comprising surface parameter values and representing a different shape;
determining, with at least one processor, an estimated position of the plurality of RF transponders on each surface model of the first plurality of surface models based on the surface model and a predetermined spatial arrangement of the plurality of RF transponders;
communicating, with an antenna of a reader device, at least one activation signal to the plurality of RF transponders arranged on the surface, the surface comprising an unknown shape;
receiving, with the antenna, a plurality of response signals from at least a subset of the plurality of RF transponders;
determining, with at least one processor, radio environment parameters for each surface model of the first plurality of surface models based on the surface parameter values, the estimated position of the plurality of RF transponders, and the plurality of response signals; and
determining, with at least one processor, at least one selected surface model of the first plurality of surface models based on the plurality of response signals and the radio environment parameters for the first plurality of surface models.

2. The method of claim 1, further comprising:
generating a second plurality of surface models based on the at least one selected surface model, each surface model of the second plurality of surface models comprising surface parameter values and representing a different shape;
determining, with at least one processor, an estimated position of the plurality of RF transponders on each surface model of the second plurality of surface models based on the surface model and the predetermined spatial arrangement of the plurality of RF transponders;
determining, with at least one processor, radio environment parameters for each surface model of the second plurality of surface models based on the surface parameter values, the estimated position of the plurality of RF transponders, and the plurality of response signals; and
determining, with at least one processor, at least one second selected surface model of the second plurality of surface models based on the plurality of response signals and the radio environment parameters for the plurality of surface models.

3. The method of claim 2, wherein the surface parameter values for the second plurality of surface models are generated by mutating and/or crosslinking the at least one selected surface model.

4. The method of claim 1, further comprising predicting a surface geometry of the unknown shape based on the at least one selected surface model or a subsequent selected surface model from a subsequent plurality of surface models.

5. The method of claim 1, further comprising randomly generating the surface parameter values for the first plurality of surface models.

6. The method of claim 5, wherein the surface parameter values for the first plurality of surface models are based on material properties of the surface.

7. The method of claim 1, wherein each surface model is represented as a function of the surface parameter values and defines at least one curve.

8. The method of claim 1, wherein the radio environment parameters comprise phase shift.

9. The method of claim 1, further comprising arranging the plurality of RF transponders on the surface as a one-dimensional or two-dimensional array.

10. A system for tracking a shape, comprising:
a plurality of radio frequency (RF) transponders arranged on a surface adapted to be formed into a plurality of shapes;
a reader device in communication with an antenna; and
at least one processor in communication with the reader device, the at least one processor programmed and/or configured to:
generate a first plurality of surface models based on the surface, each surface model comprising surface parameter values and representing a different shape;
determine an estimated position of the plurality of RF transponders on each surface model of the first plurality of surface models based on the surface model and a predetermined spatial arrangement of the plurality of RF transponders;
communicate, with the antenna, at least one activation signal to each RF transponder of the plurality of transponders arranged on the surface, the surface comprising an unknown shape;
receive, with the antenna, a plurality of response signals from at least a subset of the plurality of RF transponders;
determine radio environment parameters for each surface model of the first plurality of surface models based on the surface parameter values, the estimated position of the plurality of RF transponders, and the plurality of response signals; and
determine at least one selected surface model of the first plurality of surface models based on the plurality of response signals and the radio environment parameters for the plurality of surface models.

11. The system of claim 10, wherein the at least one processor is further programmed or configured to:
generate a second plurality of surface models based on the at least one selected surface model, each surface model of the second plurality of surface models comprising surface parameter values and representing a different shape;
determine an estimated position of the plurality of RF transponders on each surface model of the second plurality of surface models based on the surface model and the predetermined spatial arrangement of the plurality of RF transponders;
determine radio environment parameters for each surface model of the second plurality of surface models based on the surface parameter values, the estimated position of the plurality of RF transponders, and the plurality of response signals; and
determine at least one second selected surface model of the second plurality of surface models based on the plurality of response signals and the radio environment parameters for the plurality of surface models.

12. The system of claim 11, wherein the surface parameter values for the second plurality of surface models are generated by mutating and/or crosslinking the at least one selected surface model.

13. The system of claim 10, wherein the at least one processor is further programmed or configured to predict a surface geometry of the unknown shape based on the at least one selected surface model or a subsequent selected surface model from a subsequent plurality of surface models.

14. The system of claim 10, wherein the at least one processor is further programmed or configured to randomly generate the surface parameter values for the first plurality of surface models.

15. The system of claim 14, wherein the surface parameter values for the first plurality of surface models are based on material properties of the surface.

16. The system of claim 10, wherein each surface model is represented as a function of the surface parameter values and defines at least one curve.

17. The system of claim 10, wherein the radio environment parameters comprise phase shift.

18. The system of claim 10, wherein the plurality of RF transponders are arranged on the surface as a one-dimensional or two-dimensional array.

19. A computer program product for tracking a shape, wherein a plurality of radio frequency (RF) transponders are arranged on a surface adapted to be formed into a plurality of shapes, comprising at least one non-transitory computer-readable medium including program instructions that, when executed by at least one processor, cause the at least one processor to:
generate a first plurality of surface models based on the surface, each surface model comprising surface parameter values and representing a different shape;
determine an estimated position of the plurality of RF transponders on each surface model of the first plurality of surface models based on the surface model and a predetermined spatial arrangement of the plurality of RF transponders;
receive a plurality of signals from at least a subset of the plurality of RF transponders;
determine radio environment parameters for each surface model of the first plurality of surface models based on the surface parameter values, the estimated position of the plurality of RF transponders, and the plurality of signals; and
determine at least one selected surface model of the first plurality of surface models based on the first plurality of response signals and the radio environment parameters for the plurality of surface models.

20. The computer program product of claim 19, wherein the program instructions further cause the at least one processor to:
generate a second plurality of surface models based on the at least one selected surface model, each surface model of the second plurality of surface models comprising surface parameter values and representing a different shape;
determine an estimated position of the plurality of RF transponders on each surface model of the second plurality of surface models based on the surface model and the predetermined spatial arrangement of the plurality of RF transponders;
determine radio environment parameters for each surface model of the second plurality of surface models based on the surface parameter values, the estimated position of the plurality of RF transponders, and the first plurality of response signals; and
determine at least one second selected surface model of the second plurality of surface models based on the plurality of response signals and the radio environment parameters for the plurality of surface models.

* * * * *